United States Patent [19]

Boyle et al.

[11] Patent Number: 5,703,230

[45] Date of Patent: Dec. 30, 1997

[54] MESO-MONOIODO-SUBSTITUTED TETRAMACROCYCLIC COMPOUNDS AND METHODS FOR MAKING AND USING THE SAME

[75] Inventors: Ross W. Boyle; David Dolphin; Claire K. Johnson, all of Vancouver, Canada

[73] Assignee: University of British Columbia, Vancouver, Canada

[21] Appl. No.: 349,179

[22] Filed: Dec. 2, 1994

[51] Int. Cl.$^6$ .................... A61K 31/555; C07D 487/22
[52] U.S. Cl. ............................................. 540/145; 514/185
[58] Field of Search ............................................. 540/145

[56] References Cited

PUBLICATIONS

Ali et al., "Synthesis of β-Substituted Porphyrins Using Palladium Catalysed Reactions", *Tetrahedron* 50(41):11933–44 (1994).
Arnold et al., "Dimeric Porphyrins Linked by Conjugated Groups Containing Triple Bonds: the Crystal Structure of the Nickel Octaethylporphyrin Dimer Bridged by 2,5-Diethynylthiophene", *J. Chem. Soc., Chem. Commun.*, 2131–32 (1994).
DiMagno et al., "Catalytic Conversion of Simple Haloporphyrins into Alkyl-, Aryl-, Pyridyl-, and Vinyl–Substituted Porphyrins", *J. Am. Chem. Soc.* 115:2513–15 (1993).
DiMagno et al., "Facile Elaboration of Porphyrins via Metal–Mediated Cross–Coupling", *J. Org. Chem.* 58:5983–93 (1993).
Lin et al., "Highly Conjugated, Acetylenyl Bridged Porphyrins: New Models for Light-Harvesting Antenna Systems", *Science* 264:1105–11 (1994).
Lindsey et al., "Porphyrin Building Blocks for Modular Construction of Bioorganic Model Systems", *Tetrahedron* 50(30):8941–68 (1994).
Minnetian et al., "New Syntheses and Reactions of Some Halogenated Porphyrins", *J. Org. Chem*, 54:5567–74 (1989).
Samuels et al., "Halogenation of Porphin and Octaethylporphin", *J. Chem. Soc.* (C):145–47 (1967).
Sternberg et al., "An Overview of Second Generation Drugs for Photodynamic Therapy Including BPD-MA (Benzoporphyrin Derivative)", *Photodynamic Therapy and Biomedical Lasers*, 470–474 (1992).
Zhou et al., "Synthesis of β–Octasubstituted Sterically Bulky Porphyrins by Suzuki Cross Coupling", *J. Chem. Soc. Perkin Trans.* 1:2519–20 (1994).

Minnetian, O.M. et al., *Journal of Organic Chemistry*, vol. 54, No. 23 (1989), pp. 5567–5574.
Boyle, R.W. et al., *Journal of the Chemical Society, Chemical Communications*, (1995), pp. 527–528.

*Primary Examiner*—Robert T. Bond
*Attorney, Agent, or Firm*—Morrison & Foerster LLP

[57] ABSTRACT

A meso-monoiodo-substituted tetramacrocyclic compound having the formula (I):

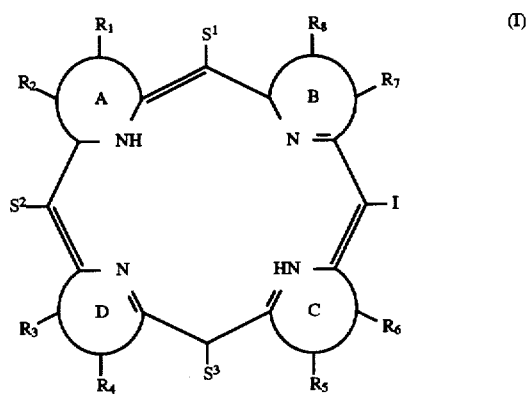

wherein:

each of A through D is independently a 5-membered, nitrogen-containing ring having the members necessary to complete a porphyrin, chlorin, bacteriochlorin or isobacteriochlorin nucleus;

$R_1$ through $R_8$ are independently a hydrogen atom, a lower alkyl group, a lower alkyl carboxylic acid or acid ester group, keto, hydroxy, nitro, amino, or a group that, taken together with another ring, ring substituent or meso-substituent, forms a fused 5- or 6-membered ring; and each of $S^1$ through $S^3$ is H, substituted or unsubstituted alkyl, substituted or unsubstituted cycloalkyl, a substituted or unsubstituted aromatic ring, or a substituted or unsubstituted heterocyclic ring. A method for synthesizing the compound comprises the step of iodinating a corresponding unhalogenated, de-metallated tetramacrocyclic compound, followed by metallating. The compound of the invention is an intermediate capable of coupling with an alkyne to achieve a desired mono-meso-alkynyl compound.

34 Claims, 5 Drawing Sheets

MESO-MONOIODO-SUBSTITUTED TETRAMACROCYCLIC COMPOUNDS AND METHODS FOR MAKING AND USING THE SAME

FIELD OF THE INVENTION

The present invention relates to certain meso-monoiodo-substituted macrocycles, their preparation and their use in synthesizing meso-monoalkynyl macrocyclic compounds. In particular, the invention relates to the iodination of meso-unsubstituted tetramacrocycles that may be or may not be substituted in some or all of the remaining three meso-positions with an alkyl or cycloalkyl group, an aromatic ring, or a heterocyclic compound. Many of these compounds are useful photosensitizers desirable in the field of photodynamic therapy ("PDT") for mediating the destruction of unwanted cells or tissues or other undesirable materials by irradiation. Others are also valuable intermediates for making other such photosensitizers.

BACKGROUND ART

In the field of PDT, various tetrapyrrolic macrocycles, such as purpurins, chlorins, bacteriochlorins, phthalocyanines and benzochlorins have shown the ability both to localize at a tumor site and to absorb light to form an activated state in response to the light. These tetramacrocycles then exhibit a cytotoxic effect on the cells or other tissues in which they are localized when irradiated at the appropriate wavelength.

To cause the desired phototoxic effect deep within a subject's tissue, however, it is necessary to use photosensitizers that possess high absorption coefficients at wavelengths longer than 650 nm, where body tissues are most transparent to light. See Sternberg et al., "An Overview of Second Generation Drugs for Photodynamic Therapy Including BPD-MA (Benzoporphyrin Derivative)", *Photodynamic Therapy and Biomedical Lasers*, 470–4 (Spinelli et al. eds. 1992). Moreover, coupling the photosensitizer with certain biological materials can enable the photosensitizer to "home" more selectively to the target tissue, less damage to surrounding normal tissues.

Meso-alkynyl substituted, tetramacrocyclic compounds have been recognized as having potentially valuable optical spectral and electrochemical properties. Lin et al., *Science*, 264, 1105–11 (1994), and Arnold et al., *J. Chem. Soc., Chem. Commun.*, 2131–32 (1994). Because of this, there has been interest in developing efficient synthetic pathways to these compounds. Previous methods of providing meso-functionalization, e.g., formylation and nitration, have required the use of harsh conditions capable of altering or destroying other functional groups on the tetramacrocyclic nucleus. Further, the established methods give access to only a single type of functional group on the tetramacrocyclic nucleus, which must subsequently be manipulated, frequently in multistep procedures, to access other useful substituents.

The 5,15-di-bromination of tetramacrocyclic compounds has been disclosed by DiMagno et al., "Facile Elaboration of Porphyrins via Metal-Mediated Cross-Coupling", *J. Org. Chem.*, 58, 5983–93 (1993), and DiMagno et al., "Catalytic Conversion of Simple Haloporphyrin into Alkyl-, Aryl-, Pyridyl-, and Vinyl-Substituted Porphyrins", *J. Am. Chem. Soc.*, 115, 2513–15 (1993). However, metal-mediated coupling reactions on brominated porphyrins have typically required the use of Schlenk inert atmosphere techniques, elevated pressures and temperatures, and sensitive Pd(O) reagents. Further, the non-porphyrin half of the couple is itself a relatively unstable zinc or tin organometallic, which must be separately prepared.

Further, while brominations and chlorinations have been performed successfully for many differently substituted porphyrins, iodinations have proved to be problematic, either yielding unstable products or requiring activation of the porphyrin nucleus with highly toxic mercury salts. When iodinated porphyrin compounds have been prepared and characterized, the iodine substituents have typically been in the β-position. See, e.g., Zhou et al., "Synthesis of β-Octasubstituted Sterically Bulky Porphyrins by Suzuki Cross Coupling", 1 *J. Chem. Soc., Perkin Trans.* 1, 2519–20 (1994).

Meso-iodophenyl tetramacrocyclic compounds have also recently been prepared by halogenation of meso-phenyl groups on a tetramacrocyclic nucleus. Lindsey et al., "Porphyrin Building Blocks for Modular Construction of Bioorganic Model Systems", *Tetrahedron*, 90:30, 3941–68 (1994), and Ali et al., "Synthesis of β-Substituted Porphyrin Using Palladium Catalysed Reactions", *Tetrahedron*, 50: 11933–44 (1994). However, none of these workers have taught the direct meso-iodination, instead of β-iodination, of a tetramacrocycle without an intervening phenyl ring. In the description of early attempts to iodinate "porphin", "octaethylporphin" and "tetraphenylporphin" by Samuels et al., "Halogenation of Porphin and Octaethylporphin", *J. Chem. Soc.*, 145–47 (1968), the resulting polyiodinated product could not be successfully isolated and/or purified. Further, the positions of the iodine substituents, when present, could not be determined.

Minnetian et al., "New Syntheses and Reactions of Some Halogenated Porphyrins", *J. Org. Chem.*, 54:5567–74 (1989), discloses the preparation of a β-iodo porphyrin compound (page 5568) and the preparation of a meso-chloro porphyrin compound (page 5570). However, no meso-iodination was observed (page 5571). Further, Minnetian et al. teaches that the site of halogenation should be determined by the size and reactivity of the halogen in question. Thus, meso-halogenation would be favored only by the smaller halogens, such as chlorine, while the larger halogens, such as bromine and iodine, should favor only β-halogenation.

Ali et al., "Synthesis of β-Substituted Porphyrin Using palladium Catalysed Reactions", *Tetrahedron*, 50: 11933–44 (1994), describes, among other things, the attempted preparation of a mono-iododeuteroporphyrin IX dimethyl ester, to be used in a subsequent coupling reaction with an alkyne. However, only an isomeric mixture of β-substituted products (3- and 8-monoiodinated) was obtained along with a 3,8-di-iodinated product. No meso-monoiodination was reported.

Despite these teachings in the art to the contrary, it has now been found that meso-monoiodination of a demetallated tetramacrocycle can be accomplished directly with the use of a suitable iodinating agent under advantageously mild conditions, even when there are no other meso-substituents or β,β'-substituents present to block competing side reactions. The resulting meso-monoiodo-tetramacrocycles are reasonably pure, thereby also providing desirably high yields.

Further, a wide range of different substituents can be introduced directly onto the tetramacrocyclic ring via a common reaction of the meso-monoiodo compound with a suitable alkynyl compound. The meso-alkynyl substituent can be widely derivatized, and the resulting substituents can include biologically active groups, such as testosterone and estradiol which are frequently susceptible to damage from elevated temperatures and/or pressures. Thus, by obviating the need for total synthesis of the tetramacrocyclic system, easy access is allowed to a wide variety of analogs from a conveniently common, pre-formed tetramacrocycle.

When the meso-alkynyl tetramacrocycle contains an aryl ring, such as a phenyl group, the ability to further derivatize these compounds provides an opportunity to fine-tune the pharmacokinetics and -dynamics of the compounds to an even greater degree. Thus, there can be made a number of related meso-substituted chlorins and bacteriochlorins exhibiting particularly desirable characteristics as PDT agents, such as bathochromically shifted Q bands and increased amphiphilicity.

DISCLOSURE OF THE INVENTION

According to the present invention, there have been prepared novel meso-monoiodo-substituted tetramacrocyclic compounds having the formula (I):

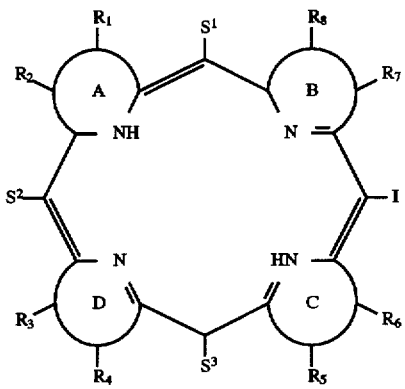

wherein:

each of A through D is independently a 5-membered, nitrogen-containing ring having the members necessary to complete a porphyrin, chlorin, bacteriochlorin or isobacteriochlorin nucleus;

$R_1$ through $R_8$ are independently a hydrogen atom, a lower alkyl group, a lower alkyl carboxylic acid or acid ester group, keto, hydroxy, nitro, amino, or a group that, taken together with another ring, ring substituent or meso-substituent, forms a fused 5- or 6-membered ring; and each of $S^1$ through $S^3$ is H, substituted or unsubstituted alkyl, substituted or unsubstituted cycloalkyl, a substituted or unsubstituted aromatic ring, or a substituted or unsubstituted heterocyclic ring.

Further, a method has been found for efficiently synthesizing the compounds of formula (I). Specifically, in the invention, a method for making a compound having formula (I) comprises the step of treating a tetramacrocycle having the formula (II):

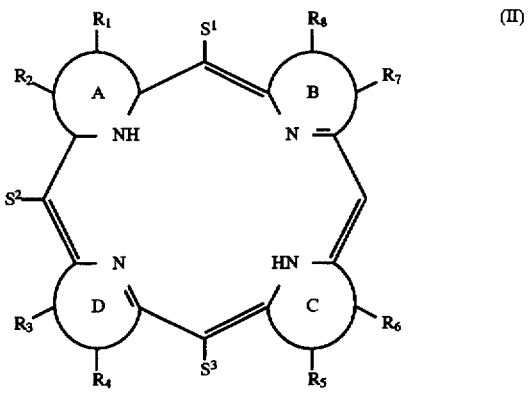

where A through D, $R_1$ through $R_8$, and $S^1$ through $S^3$ are as described above, with an iodinating agent to form the tetramacrocyclic compound of formula (I).

Further, a method of making the corresponding meso-alkynyl tetramacrocyclic compound having the formula (III):

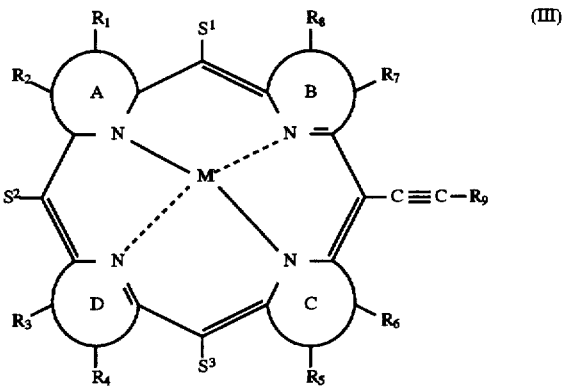

wherein M is a metal selected from the group consisting of Ni(II), Cu(II), Zn, Sn, Ge, Si, Ga, Al Mn(III), Gd(III), In and Tc;

each of A through D, $R_1$ through $R_8$, and $S^1$ through $S^3$ are the same as described above; and $R_9$ is an organometallic radical, a substituted or unsubstituted alkyl group having from 1 to 30 carbon atoms, an aromatic ring, a heterocyclic ring, or a biological substrate;

comprises the steps of:

a. treating a tetramacrocyclic compound having the formula (II), as described above, with an iodinating agent to form the corresponding meso-monoiodo-substituted compound of formula (I);

b. metallating the meso-monoiodo-substituted compound to form the corresponding metallated compound; and b. alkynylating the metallated compound in the presence of an alkyne having the formula

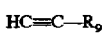

to give the meso-alkynyl tetramacrocyclic compound of formula (III).

BRIEF DESCRIPTION OF DRAWINGS

The present invention will be more clearly understood by referring to the following drawings, in which.

MODES OF CARRYING OUT THE INVENTION

Figure 1:
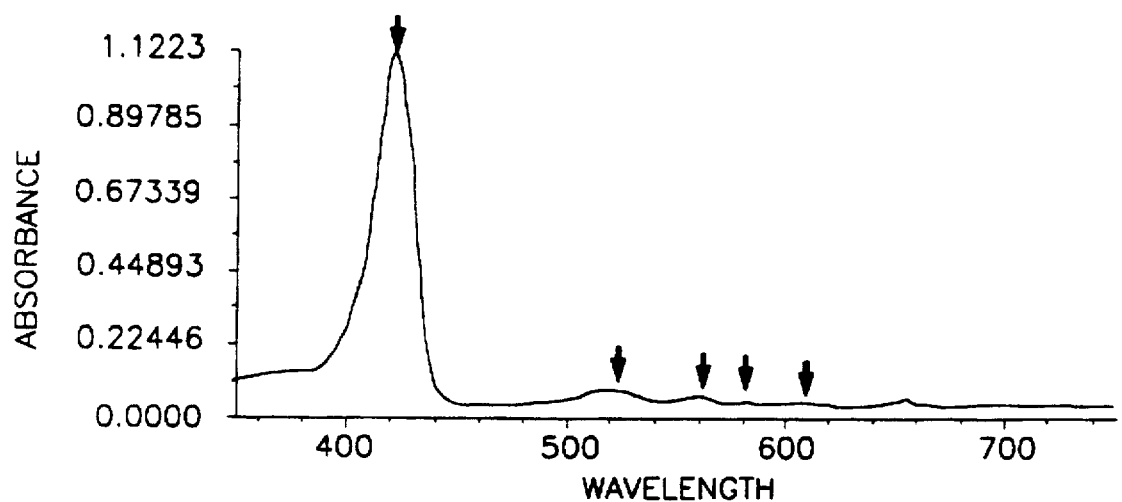
FIG. 1 shows the electronic absorption spectrum for 10-iodo-5,15-diphenylporphyrin.

The meso-monoiodo-substituted tetramacrocyclic compounds of the invention have formula (I), as described and shown above.

Each of A through D can independently be any 5-membered, nitrogen-containing ring having the members necessary to complete a porphyrin, chlorin, bacteriochlorin or isobacteriochlorin nucleus, such as those having the structures:

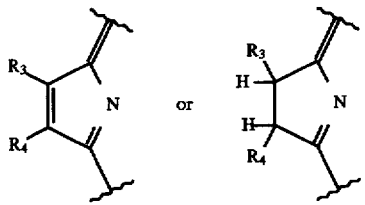

Preferably, however, each ring, A through D, has one of the above two structures.

$R_1$ through $R_8$ can be any one of a large number of ring substituents, so long as they do not interfere with the iodination, metallation or coupling reactions outlined above. Preferably, $R_1$ through $R_8$ are independently a hydrogen atom; a lower alkyl group, such as methyl, ethyl, n-propyl, isopropyl, t-butyl and n-pentyl; a lower alkyl carboxylic acid, such as formyl, carboxymethyl, carboxyethyl, carboxy-n-butyl, carboxy-sec-butyl, carboxy-n-hexyl; a carboxylic acid ester group, such as $-CH_2CH_2COOCH_3$, $-CH_2CH_2COOCH_2CH_3$, $-CH_2CH(CH_3)COOCH_2CH_3$, $-CH_2CH_2CH_2COOCH_2CH_2CH_3$, $-CH_2CH(CH_3)_2COOCH_2CH_3$; keto; hydroxy; nitro; amino; or the like.

Further, $R_1$ and $R_2$, $R_3$ and $R_4$, $R_5$ and $R_6$, or $R_7$ and $R_8$, can be taken together with another ring, ring substituent or meso-substituent to form a fused 5- or 6-membered ring. The fused 5- or 6-membered ring so formed may be any saturated or unsaturated, carbocyclic or heterocyclic 5- or 6-membered ring that does not interfere with the iodination, metallation or coupling reactions of the invention. Examples of such rings include cyclopentane, furan, thiophene, pyrrole, isopyrrole, 3-isopyrrole pyrazole, 2-isoimidazole, 1,2,3-triazole, 1,2,4-triazole, 1,2-dithiole, 1,3-dithiole, 1,2, 3-oxathiole, isoxazole, oxazole, thiazole, isothiazole, 1,2,3-oxadiathiazole, 1,2,4-oxadiazole, 1,2,5-oxadiazole, 1,3,4-oxadiazole, 1,2,3-dioxazole, 1,2,4-dioxazole, 1,2,5-oxathiazole, 1,3-oxathiole, benzene, cyclohexane, 1,2-pyran, 1,4-pyran, 1,2-pyrone, 1,4-pyrone, 1,2-dioxin, 1,3-dioxin (dihydro form), pyridine, pyridazine, pyrimidine, pyrazine, piperazine, 1,3,5-triazine, 1,2,4-triazine, 1,2,4-oxazine, 1,3,2-oxazine, o-isoxazine, 1,2,5-oxathiazine, 1,4-oxazine, p-isoxazine, 1,2,6-oxathiazine, 1,3,5,2-oxadiazine, morpholine, azepine, oxepin, thiepin, 1,2,4-diazepine, and the like. Preferably, when $R_1$ and $R_2$, $R_3$ and $R_4$, $R_5$ and $R_6$, or $R_7$ and $R_8$, form a fused, 5- to 6-membered ring, the ring is a 6-membered ring. Most preferably, when $R_1$ and $R_2$, $R_3$ and $R_4$, $R_5$ and $R_6$, or $R_7$ and $R_8$, form a ring, it is a 6-membered carbocyclic ring, i.e., a benzene ring.

In a particularly preferred embodiment, $R_1$ through $R_8$ are independently hydrogen, methyl, ethyl, or lower alkyl esters, most preferably being hydrogen, methyl or ethyl.

In yet another preferred embodiment, A through D and $R_1$ through $R_8$ have the members necessary to make a porphyrin, chlorin, bacteriochlorin, benzochlorin, hydroxychlorin or hydroxybacteriochlorin nucleus.

$S^1$ through $S^3$ are the same or different and can be H, any one of a large number of substituted or unsubstituted alkyl groups, substituted or unsubstituted cycloalkyl groups, substituted or unsubstituted aromatic rings or substituted or unsubstituted heterocyclic rings. When one or more of $S^1$ through $S^3$ is an alkyl group, it preferably has from about 1 to about 18 carbon atoms, more preferably about 1 to 12 carbon atoms and, even more preferably, about 1–6 carbon atoms. Examples of typical alkyl groups are methyl, ethyl, isopropyl, sec-butyl, tert-butyl, n-pentyl and n-octyl.

When one or more of $S^1$ through $S^3$ is an alkyl group, it may be unsubstituted or substituted with any group that does not interfere with other reactions of the invention, such as the iodination reaction. For example, when one or more of $S^1$ through $S^3$ is an alkyl group, it may be substituted by a halogen atom, such as fluorine, chlorine or bromine; a hydroxy group, such as in pentoses and hexoses; thiol; a carbonyl group, such as when the alkyl group is an aldehyde, ketone, carboxylic acid (e.g., a fatty acid) or ester or amide; a primary, secondary, tertiary, or quaternary amino group; nitrile; a phosphate group; a sulfonate group; or other similar groups.

When one or more of $S^1$ through $S^3$ is a cycloalkyl group, it preferably contains from about 3 to about 7 carbon atoms. Examples of typical cycloalkyl groups include cyclopropyl, cyclohexyl, and cycloheteroalkyl, such as glucopyranose or fructofuranose sugars. When one or more of $S^1$ through $S^3$ is a cycloalkyl group, it may be unsubstituted or substituted with any group that does not interfere with the iodination reaction. For example, when one or more of $S^1$ through $S^3$ is a cycloalkyl group, they may be substituted by any of the same substituents described above for the case when one or more of $S^1$ through $S^3$ is an alkyl group.

When one or more of $S^1$ through $S^3$ is an aryl group, it preferably contains from about 5 to about 12 carbon atoms, optionally containing one or more rings that are fused to the existing conjugated porphyrin ring structure. Examples of suitable aromatic rings include phenyl, naphthyl, anthracenyl and the like.

Examples of useful heterocyclic rings include furan, thiophene, pyrrole, isopyrrole, 3-isopyrrole, pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxathiazole, 1,3-oxathiole, benzene, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,6-oxazine, 1,4- oxazine, o-isoxazine, p-isoxazine, 1,2,5-oxathiazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, naphthalene, 1,2-benzopyran, 1,2-benzopyrone, 1,4-benzopyrone, 2,1-benzopyrone, 2,3-benzopyrone, quinoline, isoquinoline, 1,2-benzodiazine, 1,3-benzodiazine, naphthyridine, pyrido[3,4-b]-pyridine, pyrido[3,2-b]-pyridine, pyrido[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, anthracene, phenanthrene, carbazole, xanthene, acridine, purine.

In another embodiment, at least one of $S^1$ through $S^3$ has the structure:

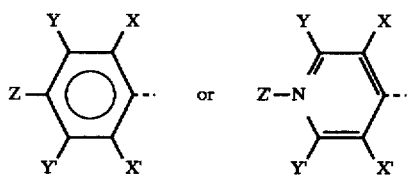

wherein X, Y, Z, X', Y' and Z' can be any one of a large number of substituents and are generally used to "fine tune" the biological activity, the biodistribution, the absorption and clearance characteristics, and the physical properties of the desired product. One way in which this may be done by selecting substituents in such a manner that the compound of formula (I) or (II) is an amphiphilic molecule. By "amphiphilic" is meant the molecule becomes more asymmetric, such as (1) having both (a) a highly polar, water-soluble region and (b) a highly hydrophobic, water-insoluble region;
(2) having both (a) a nonionic region and (b) an ionic region; or
(3) having both (a) an anionic portion and (b) a cationic portion.

However, it should be noted that the invention also includes meso-trisubstituted tetramacrocyclic compounds having substantially or exactly identical aryl or heterocyclic meso-substituents. Further, any aryl or heterocyclic meso-substituent chosen should also have no adverse effect on the ability of the compound to undergo the iodination step or other reactions used to prepare the compounds of the invention.

Preferably, X, X', Y, Y' and Z are independently (1) hydrogen; (2) halogen, such as fluoro, chloro, iodo and bromo; (3) lower alkyl, such as methyl, ethyl, n-propyl, isopropyl, t-butyl, n-pentyl and the like groups; (4) lower alkoxy, such as methoxy, ethoxy, isopropoxy, n-butoxy, t-pentoxy and the like; (5) hydroxy; (6) carboxylic acid or acid salt, such as —CH$_2$COOH, —CH$_2$COO—Na$^+$, —CH$_2$CH(Br)COOH, —CH$_2$CH(CH$_3$) COOH, —CH(Cl)—CH$_2$—CH(CH$_3$)—COOH, —CH$_2$—CH$_2$—C(CH$_3$)$_2$—COOH, —CH$_2$—CH$_2$—C(CH$_3$)$_2$—COO$^-$K$^+$, —CH$_2$—CH$_2$—CH$_2$—CH$_2$—COOH, C(CH$_3$)$_3$—COOH, CH(Cl)$_2$—COOH and the like; (7) carboxylic acid ester, such as —CH$_2$CH$_2$COOCH$_3$, —CH$_2$CH$_2$COOCH$_2$CH$_3$, —CH$_2$CH(CH$_3$)COOCH$_2$CH$_3$, —CH$_2$CH$_2$CH$_2$COOCH$_2$CH$_3$, —CH$_2$CH(CH$_3$)$_2$COOCH$_2$CH$_3$, and the like; (8) sulfonic acid or acid salt, for example, group I and group II salts, ammonium salts, and organic cation salts such as alkyl and quaternary ammonium salts; (9) sulfonic acid ester, such as methyl sulfonate, ethyl sulfonate, cyclohexyl sulfonate, p-tosylate, o-tosylate and the like; (10) phosphoric acid, phosphato or phosphate ester, such as O-ethyl phosphate, O-O-diethyl phosphate, or O-ethyl phosphonic acid; (11) amino, such as unsubstituted primary amino, methylamino, ethylamino, n-propylamino, isopropylamino, 5-butylamino, sec-butylamino, dimethylamino, trimethylamino, diethylamino, triethylamino, di-n-propylamino, methylethylamino, dimethyl-sec-butylamino, 2-aminoethanoxy, ethylenediamino, 2-(N-methylamino) heptyl, cyclohexylamino, benzylamino, phenylethylamino, anilino, N-methylanilino, N,N-dimethylanilino, N-methyl-N-ethylanilino, 3,5-dibromo-4-anilino, p-toluidino, diphenylamino, 4,4'-dinitrodiphenylamino and the like; (12) cyano; (13) nitro; (14) a biologically active group; or (15) any other substituent that increases the amphiphilic nature of the compound of formula (I) or (II).

The term "biologically active group" can be any group that selectively promotes the accumulation, elimination, binding rate, or tightness of binding in a particular biological environment. For example, one category of biologically active groups is the substituents derived from sugars, specifically, (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, sorbose, and tagatose; (3) pyranoses such as glucopyranose; (4) furanoses such as fructofuranose; (5) O-acyl derivatives such as penta-O-acetyl-α-glucose; (6) O-methyl derivatives such as methyl α-glucoside, methyl β-glucoside, methyl α-glucopyranoside, and methyl-2,3,4,6-tetra-O-methyl-glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, δ-gluconolactone, δ-glucuronolactone, ascorbic acid, and dehydroascorbic acid; (10) phosphoric acid esters such as α-glucose 1-phosphoric acid, α-glucose 6-phosphoric acid, α-fructose 1,6-diphosphoric acid, and α-fructose 6-phosphoric acid; (11) deoxy sugars such as 2-deoxy-ribose, rhamnose (deoxymannose), and fucose (6-deoxy-galactose); (12) amino sugars such as glucosamine and galactosamine; muramic acid and neuraminic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as α-amylose, amylopectin, dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides, particularly those known to have affinity for specific receptors, for example, oxytocin, vasopressin, bradykinin, LHRH, thrombin and the like.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. The term "ligand specific for a receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; and (4) neurotransmitters, such as acetylcholine, serotonin, dopamine, and the like. Any analog of these substances that also succeeds in binding to a biological receptor is also included.

Particularly useful examples of substituents tending to increase the amphiphilic nature of the compound of formula (I) include: (1) long chain alcohols, for example, —$C_{12}H_{24}$—OH where —$C_{12}H_{24}$ is hydrophobic; (2) fatty acids and their salts, such as the sodium salt of the long-chain fatty acid oleic acid; (3) phosphoglycerides, such as phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidal choline; (4) sphingolipids, such as sphingomyelin; and (5) glycolipids, such as glycosyldiacylglycerols, cerebrosides, sulfate esters of cerebrosides or gangliosides.

In a preferred embodiment, X, X', Y, Y' and Z are independently hydrogen, halogen, lower alkyl, lower alkoxy, hydroxy, carboxylic acid or acid salt, carboxylic acid ester, sulfonic acid or acid salt, sulfonic acid ester, substituted or unsubstituted amino, cyano, nitro, or a biologically active group, and Z' is hydrogen or lower alkyl. In another embodiment, X, Y, X' and Y' are each hydrogen, and Z is selected from the group consisting of hydrogen, halogen, lower alkyl, lower alkoxy, hydroxy, carboxylic acid, carboxylic acid ester, sulfonic acid ester (especially aromatic sulfonic acid ester), nitro, amino (especially lower alkyl amino), cyano, and a biologically active group.

In yet another embodiment, X, Y, Z, X' and Y' are selected from the group consisting of hydrogen, methyl, ethyl, t-butyl, methoxy, hydroxy, OR where R is an alkyl group or a fatty acid group having from 6 to 18 carbon atoms, fluoro, chloro, iodo, bromo, —C(O)—OCH$_3$, cyano, nitro, or a ligand specific for a biological receptor. In a further preferred embodiment, X, X', Y and Y' and Z is selected from the group consisting of hydrogen, halogen, lower alkyl, lower alkoxy, hydroxy, carboxylic acid or acid salt, carboxylic acid ester, sulfonic acid ester, sulfonic acid or acid salt, nitro, amino, cyano, and a biologically active group. In still another preferred embodiment, at least one of X, Y, Z, X' and Y' is a biologically active group or a substituent that increases the amphiphilic nature of the molecule.

In a particularly preferred embodiment, $S^1$ through $S^3$ are selected from the group consisting of phenyl, naphthyl, pyridinyl, lower N-alkyl pyridinium salts, indolyl, pyrazinyl, pyrimidinyl, imidazolyl, triazolyl, pyrrolyl, pyrazolyl, pyridazinyl, indolizinyl, furanyl, thiophenyl and steroids. Even more preferably, S through $S^3$ are identical.

A particularly preferred specific example of the meso-monoiodo tetramacrocyclic compounds of the invention is:

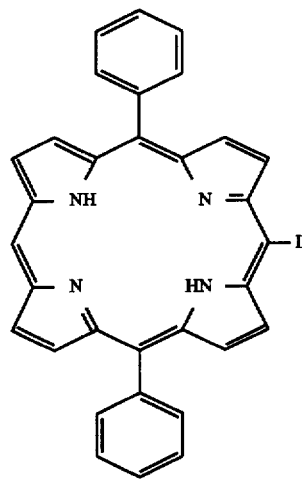

The process of making the meso-monoiodo compounds of the invention comprises treating a tetramacrocycle of formula (II) with an appropriate iodinating agent. The starting tetramacrocycle of formula (II) for this reaction can be prepared by any one of a number of standard procedures. Examples include such techniques as:

(1) Pyrrole and appropriately substituted aldehydes can be prepared by the Adler method, in accordance with Adler et al., "A Simplified Synthesis for meso-Tetraphenylporphyrin", *J. Org. Chem.*, 32, 476 (1967), or by the Lindsey method, as described in "Investigation of a Synthesis of meso-Porphyrins Employing High Concentration Conditions and an Electron Transport Chain for Aerobic Oxidation", *J. Org. Chem.*, 59, 579-87 (1994). Similar reactions are described for meso-alkyl compounds in "Facile Syntheses of Tetraalkylchlorin and Tetraalkylporphyrin Complexes and Comparison of the Structures of the Tetramethylchlorin and Tetramethylporphyrin Complexes of Nickel (II), *J. Am. Chem. Soc.*, 102:6852-54 (1980).

(2) The condensation of dipyrrolic compounds and their counterparts, as described by Wallace et al., "Rational Tetraphenylporphyrin Syntheses: Tetraarylporphyrins from the MacDonald Route", *J. Org. Chem.*, 58, 7245-47 (1993).

(3) The manipulation of a porphyrin at its β- or meso-positions, for example, as described by DiMagno et al., "Facile Elaboration of Porphyrins Via metal-Mediated Cross-Coupling", *J. Org. Chem.*, 58, 5983-93 (1993); or by Osuka et al., "Synthesis of 5,15-Diaryl-Substituted Oxochlorins from 5,15-Diaryl-octaethyl Porphyrin, *Bull. Chem. Soc. Japan*, 66, 3837-39 (1993); or the manipulation of substituents on a pre-existing and appropriately meso-substituted phenylporphyrins described by Hombrecher et al., "An Efficient Synthesis of Tetraaryl Porphyrins Substituted with Ester Groups Bearing Long Alkyl Chains", *Tetrahedron*, 49:12, 2447-56 (1993). The disclosures of all of the above documents are hereby incorporated by reference.

The compound of formula (III) used as the starting material for the iodination reaction can be prepared by any one of several known synthetic routes. One general procedure for carrying out such a reaction is as follows: Typically, an equimolar mixture of dipyrromethane and an appropriately substituted aldehyde are reacted under a nitrogen atmosphere with acid catalysis. Oxidation of the formed porphyrinogen with air or treatment with DDQ as an oxidant gives the porphyrin, which is then typically purified by column chromatography. Preferably, the compound of formula (II) is prepared by using the method described by Manka et al., *Tetrahedron Letters*, 30(50), 6989 (1989), which is hereby incorporated by reference.

The iodination reaction of the invention is carried out by treating the starting material with an iodinating agent. Any one of a large number of iodinating agents can be used, so long as it does not modify or interfere with any of the other substituents present on the compound of formula (II). Examples of suitable iodinating agents include $I_2$; silver triiodoacetate; tris(triiodoacetoxy) thallium; mixtures of iodine, nitric acid and sulfuric acid; mixtures of iodine and iodic or periodic acid; mixtures of iodine and bis (trifluoroacetoxy) iodobenzene; diacetoxyphenyl iodide; N-iodoamides, such as N-iodoacetamide, N-iodo-4-nitrobenzamide, N-iodo-2,4-dinitrobenzamide and N-iodosuccinimide; iodinate substrates that are activated toward electrophilic substitution or mildly deactivated substrates such as iodobenzenes; mixtures of iodine, potassium permanganate and sulfuric acid; iodine-metal mixtures such as iodine/silver(I), iodine/copper(II), iodine/lead(IV) or iodine/antimony(V); mixtures of potassium, sodium or an ammonium iodide in trifluoroacetic acid with a metal salt such as cobalt(III), manganese(III) or cerium(IV); combinations thereof; and the like. Preferably, the iodinating agent is selected from the group consisting of bis(trifluoroacetoxy) iodobenzene, $I_2$, N-iodosuccinimide, diacetoxyphenyl iodine, silver triiodoacetate, tris(triiodoacetoxy) thallium, and combinations thereof. A particularly preferred iodinating agent is either N-iodosuccinimide or bis (trifluoroacetoxy) iodobenzene used in combination with iodine.

The amount of the iodinizing agent is generally stoichiometric, and typically varies from about 0.75 to about 1.5 equivalents of iodine per mole of starting tetramacrocycle. Preferably, the amount of iodinizing agent used is about 1.0 equivalent per mole of starting material.

While the iodinizing agent can be added to a reaction mixture neat, especially when it is a liquid at room temperature, it is best used dissolved in a suitably non-reactive solvent. When used, the choice of a solvent depends on the substituent pattern on the tetramacrocyclic starting material, which affects its solubility. However typically encountered solvents include aromatic solvents, such as pyridine, toluene and benzene; chlorinated solvents, such as $CHCl_3$, dichloromethane and 1,1-dichloroethane; water; ethers, such as diethyl ether, tetrahydrofuran, diethylene glycol and glycol dimethyl ether (ethylene glycol dimethyl ether); ketones such as acetone and pinacolone; acetonitrile; DME, DMF and DMSO; and mixtures thereof.

When the starting material is water-soluble, the preferred solvent is water. When an organic solvent is used, particularly useful solvent systems include combinations of chlorinated solvents, such as $CHCl_3$ and dichloromethane, mixed with about 2–25 volume % pyridine. Most preferably, the solvent is a mixture of pyridine and chloroform.

The temperature of the reaction mixture during iodination can vary widely but, typically, is maintained at room temperature or cooled somewhat to a temperature in the range of about −10° C. to room temperature. Preferably, the reaction is carried out at about room temperature.

The time required for the iodination reaction of the invention will depend to a large extent on the temperature used and the relative reactivities of the starting materials. Particularly when the meso-substituents are aryl or a bulky alkyl group, such as tert-butyl, the reaction time tends to be relatively slow due to steric hindrance of the β-positions against the attack of the incoming iodide radical. Thus, even though di-mesophenyl-substituted systems have been observed to react relatively quickly, the tri-substituted systems, at least where one or more of $S^1$ through $S^3$ are particularly bulky such as a tert-butyl group, a cycloalkyl group, or a substituted phenyl ring, may require a significantly longer time to go to completion. Therefore, the reaction time can vary greatly, for example, from about 10 minutes to about 7 days. Preferably, the time required for the iodination reaction is in the range of about one to two hours.

The iodination reaction can be carried out at pressures both above and below atmospheric pressure. Preferably, however, the reaction is carried out at a pressure about equal to atmospheric pressure.

The iodination step of the invention can be carried out under conditions of normal, ambient lighting. However, because the substrates and products of the iodination are often good photosensitizers, the exclusion of light is sometimes preferred to minimize side reactions.

Techniques such as various types of chromatography, especially thin layer chromatography (TLC) and HPLC, can be used to follow the progress of the reaction by the disappearance of the starting tetramacrocycle. At the conclusion of the iodination reaction, a reaction mixture results, from which the mono-iodo product can be separated and purified by any conventional means, typically chromatographically. Although the iodination reaction mixture can be used directly in the metallation, alkynylation, or other subsequent reaction step without the intervening isolation or purification, it is preferable to isolate and/or purify the iodinated compound to minimize the ease of product isolation and/or purification further down the synthetic pathway.

In any event, the mono-iodinated compound, e.g., $H_2DPPI$ (5,15-diphenylporphyrin) may be used as intermediates to make a wide variety of other compounds. Examples of useful reagents and corresponding products for $H_2DPPI$ are shown in the table below:

| Reagent to be Reacted with $H_2DPPI$ | Product Expected |
|---|---|
| A/Cu | $H_2DPP-H_2DPP$ |
| Ar—Cu | $H_2DPP-Ar$ |
| $Alk_2LiCu$ | $H_2DPP-Alk$ |
| $R-C\equiv C-Cu$ | $H_2DPP-C\equiv C-R$ |
| $CF_3CO_2Na/CuI$ | $H_2DPP-CF_3$ |
| $C_nF_{2n-1}Cu$ | $H_2DPP-C_nF_{2n-1}$ |
| $NaCH(CO_2Et)_2/CuI$ | $H_2DPP-CH_2-CO_2H$ |
| CuCN | $H_2DPP-CN$ |
| $NaCHCNCO_2Et/CuI$ | $H_2DPP-CH_2-CN$ |
| PhSNa/CuI | $H_2DPP-S-Ph$ |
| $CF_3SCu$ | $H_2DPP-S-CF_3$ |
| CuSCN | $H_2DPP-S-S-H_2DPP$ |
| ArSeK/CuI | $H_2DPP-Se-Ar$ |
| KSeCN/CuI | $H_2DPP-Se-CN$ |
| $P(OEt)_3/CuCl$ | $H_2DPP-\overset{O}{\underset{\|}{P}}(OEt)_2$ |
| $P(Ar)_3/CuI$ | $(H_2DPP)_4P^+I^-$ |
| $Cl_2$ | $H_2DPP-ICl_2$ |
| $XeF_2$ | $H_2DPP-IF_2$ |
| [O] | $H_2DPP-IO$ |
| $RCO_3H$ | $H_2DPP-I(OCOR)_2$ |
| PhH/HX/[O] | $H_2DPP-I-Ph$ |
| hv/PhH | $H_2DPP-Ph$ |
| "Ni" | $H_2DPP-H_2HDPP$ |

-continued

| Reagent to be Reacted with H$_2$DPPI | Product Expected |
|---|---|
| "Pd" { ArMgBr | H$_2$DPP—Ar |
| ArZnCl | H$_2$DPP—Ar |
| ArCu | H$_2$DPP—Ar |
| "Pd" { CH$_2$=CH$_2$ | H$_2$DPP—CH=CH$_2$ |
| Me$_3$SnCH=CH$_2$ | H$_2$DPP—CH=CH$_2$ |
| Me$_3$SiCH=CH$_2$ | H$_2$DPP—CH=CH$_2$ |
| R—CH=CH$_2$/"Pd" | H$_2$DPP—CH=CH—R |
| Bu$_4$N$^-$Br$^-$/"Ni" | H$_2$DPP—Br |
| CO/H$_2$/"Pd" | H$_2$DPP—CHO |
| CO/AlkOH/"Pd" | H$_2$DPP—CO$_2$Alk |
| CO/Et$_3$Sn$_2$/"Pd" | H$_2$DPP—C(=O)—C(=O)—H$_2$DPP |
| CH$_2$=CH—C(=O)—R | H$_2$DPP—CH=CH—C(=O)—R |

For more information regarding the details of these reactions, see Merkushev, "Advances in the Synthesis of Iodoaromatic Compounds", *Synthesis*, 923–37 (1988).

Where the meso-alkynyl-substituted tetramacrocyclic compound of formula (III) is desired, the iodinated product having formula (I) should be metallated. The metallation step should take place between the iodination and alkynylation coupling reaction, since iodination of the starting tetramacrocycle is facilitated when the metal is not present, and the progress of the alkynylation step is strongly facilitated when a metal is present. In many cases, having a metal ion present increases the solubility of the iodinated intermediate, thus enabling a higher concentration of reactants and a shorter reaction time for the alkynylation step.

Suitable metallating reagents and conditions are widely known by those of ordinary skill in the art. Specifically, any metal salt used in combination with a polar solvent that is capable of metallating is suitable. However, the M in formula (III) (and thus the metal in the metal salt) can be any metal species that is capable of forming a metal complex with a compound of formula (II), and is preferably selected from the group consisting of Ni(II), Cu(II), Zn, Sn, Ge, Si, Ga and Al.

Examples of useful metal salts include zinc(II) acetate, Ni(II) acetate, Ni(II) "ACAC" (acetylacetone), Cu(II) acetate, Cu(II) ACAC, Sn(II) chloride, Sn(IV) chloride, gallium triacetate [Ga(OAc)$_3$], germanium tetrachloride (GeCl$_4$), gadolinium triacetate [Ga(OAc)$_3$], aluminum trichloride (AlCl$_3$), Mn(OAc)$_3$, silicon tetrachloride (SiCl$_4$) and the like. The use of strongly oxidizing metal salts should be avoided because they can adversely affect the stability of the macrocycle. Preferably, the metal salt is selected from the group consisting of Zn(OAc)$_2$, Cu(OAc)$_2$, Ni(OAc)$_2$, SnCl$_2$, SnCl$_4$ and Gd(OAc)$_3$.

The above metallating agents are preferably used in combination with a suitably non-reactive solvent. Examples of useful solvents include water; alcohols, such as ethanol, methanol, iso-propanol and the like; haloalkanes such as chloroform, methylene chloride, 1,1-dichloroethane and the like; nitrogen-containing solvents such as pyridine, dimethylformamide, tetrahydrofuran and the like; relatively unreactive aromatic compounds such as benzene, toluene and the like; ethers such as diethyl ether, diethylene glycol, and glycol dimethyl ether; and the like. Most preferably the organic solvent is methanol, chloroform, pyridine, CH$_2$Cl$_2$, dichloroethane, or a mixture of any two or three of these solvents.

The metallating conditions should be selected to be compatible with the particular substituents present on the iodinated, tetramacrocyclic compound being metallated. The temperature of the reaction mixture during the metallating process can vary widely but, typically, is maintained in the range of about 0° to 120° C. For example, refluxing methanol can be used in some circumstances, which would provide a temperature of about 65° C. However, the metallating reaction is most preferably carried out at about room temperature or below.

The time required for metallation varies widely, depending on the temperature used and the relative reactivities of the starting materials, particularly the metallating agent. For example, when Zn(OAc)$_2$ is used as the metallating agent in a mixture of methanol and chloroform as a solvent, the reaction typically takes place from about 12 to 24 hours, most often in about a 16-hour period.

Preferably, effective metallating conditions can be quite mild. A particularly preferred set of conditions is a 400% excess of Zn(OAc)$_2$ in a mixture of 1:10 methanol:chloroform at 80°C. for 16 hours.

The reaction can be carried out above or below atmospheric pressure. Preferably, the reaction is carried out at a pressure about equal to atmospheric pressure. The reaction can be carried out in the presence of a mixture of gases approximating air but, when particularly reactive reactants are involved, the gaseous mixture may be enriched with an inert gas, such as nitrogen gas, argon, and the like.

Straightforward procedures can be used to isolate the metallated product, such as extraction with any immiscible liquid, eluting on a silica gel column or other type of chromatography, drowning out in a non-solvent, precipitating out or otherwise crystallizing, evaporation of solvent, or some combination of these or other conventional methods. Preferred methods of isolating the desired metallated compound include chromatography and/or crystallization.

If further purification of the metallated product is desired, it may be subjected to additional purification procedures, such as recrystallization, eluting on a silica gel chromatography column, and combinations of these methods. Although the iodination reaction mixture can be used directly in the metallation, alkynylation, or other subsequent reaction step without the intervening isolation or purification, it is preferable to isolate and/or purify the iodinated compound to minimize the ease of product isolation and/or purification further down the synthetic pathway.

Because metallation reactions are known to those of ordinary skill in this art, additional information can be obtained in J. W. Buchler, "Synthesis and Properties of Metalloporphyrins", The Porphyrins, Vol. I, Chapter 10 (2978), which is hereby incorporated by reference.

The metallated product is advantageously coupled with a terminal alkyne to form the corresponding meso-alkynyl tetramacrocycle of formula (III). Examples of useful alkynes include 3-butyn-1-ol, 4-phenyl-1-butyne, 3,3-diethoxy-1-propyne, 3-trimethylsilyl-1-propyne, long-chain alkynes of about 6 to 12 carbon atoms such as 1,7-octadiyne and 1-decyne, 3-propynyl steroids and sterols, propargyl bromide, propargyl chloride, a propargyl alcohol, propargyl nitrile, propargyl amine, propargyl acetate, propargyl tosylate, and the like. Particularly preferred alkynes are of the formula HC≡CH where R is —C$_6$H$_5$, —CH(OC$_2$H$_5$)$_2$, Si(CH$_3$)$_3$, testosterone or estradiol.

Typically, the alkynylation process takes place in the presence of a catalyst such as Pd(PPh$_3$)$_2$Cl$_2$, CuI, Pd(II) OAc, Pd(PPh$_3$)$_4$, and the like. However, particularly convenient catalysts include Pd(PPh$_3$)$_2$Cl$_2$, CuI, and Pd(II)OAc. Most preferably the catalyst is a combination of Pd(PPh$_3$)$_2$Cl$_2$ and CuI.

An organic base usually used in the alkynylation reaction mixture as a scavenger. A useful organic base is generally one that is a strong base but a weak nucleophile and that, thereby, speeds up the formation of the desired product. Preferred bases include pyridine, imidazole, isoquinoline, tert-alkyl amines such as trimethylamine, triethylamine, methylsulfonamide, and the like. The amount of base used can vary widely, so long as a sufficient amount is present to neutralize the HI released during the course of the coupling reaction. Preferably, however, the amount of base used falls within the range of about 2 to about 20 equivalents. Some bases, such as triethylamine or pyridine, can also be used as solvents or co-solvents for the iodination and/or metallation reactions.

Most of the above alkynes are used in combination with a suitably non-reactive organic solvent, such as methanol, ethanol, tetrahydrofuran, DMF, DMSO, and the like, to aid in solubilizing the meso-alkenyl product, especially when the product is an anionic or cationic species.

A particularly preferred combination of catalyst, base, and solvent for the alkynylation reaction of the invention is $Pd(PPh_3)_2Cl_2$ and CuI in a mixture of THF and triethylamine.

The temperature of the reaction mixture during the alkynylation reaction can vary widely depending upon the catalyst and solvent system being used. For example, when $Pd(PPh_3)_2Cl_2$ is being used as the catalyst, the temperature is typically allowed to remain at about room temperature. When other catalysts are used, however, the temperature can range from about 1° to about 100° C.

The time required for the alkynylation reaction of the invention will depend to a large extent on the temperature used and the relative reactivities of the starting materials but, preferably, is about one to twelve hours. The alkynylation reaction can be carried out in the presence of gases at a pressure both above and below atmospheric pressure. Most frequently, however, the reaction is carried out at a pressure about equal to atmospheric pressure.

The resulting product, a meso-alkynyl tetramacrocycle of formula (III), can be isolated by any conventional method, such as by drowning out in a non-solvent, precipitating out, extraction with any immiscible liquid, evaporation of a solvent, or some combination of these or other conventional methods. Typically, the meso-alkynyl compound of formula (III) may then be purified by any one or a combination of known purification techniques, such as recrystallization, various forms of chromatography (e.g. silica/$CH_2Cl_2$-0.5% MeOH), trituration with a non-solvent or a partial solvent, vacuum distillation, countercurrent extraction techniques, and the like.

A general procedure for coupling of acetylenic derivatives with meso-monoiodo tetramacrocycle compounds is as follows:

A known amount of a meso-monoiodo tetramacrocycle is dissolved in dry triethylamine or tetrahydrofuran. If the iodide is not sufficiently soluble in triethylamine, a appropriate amount of dimethylformamide or an additional amount of tetrahydrofuran may also be added. Then bis(triphenylphosphine)palladium(II) chloride, copper(I) iodide, and a 2-3 molar excess of the alkyne to be coupled, are added under a nitrogen atmosphere, stirring either at room temperature or with heat as required. The course of the reaction is monitored by TLC. The solution is heated or left at room temperature for a time from about one to about 48 hours, typically about two hours. After completion of the reaction, the solvent is evaporated off under reduced pressure. The residue is chromatographed, for example, on silica gel.

The meso-alkynyl tetramacrocycle compounds of the invention are useful as photosensitizers used in photodynamic therapy (PDT), as well as being synthetic intermediates for making related photosensitizers. As photosensitizers, the compounds of the invention are useful in sensitizing neoplastic cells or other abnormal tissues to destruction by irradiation with visible light. Upon photoactivation, the energy of photoactivation is believed to be transferred to endogenous oxygen, thus converting it to singlet oxygen. This singlet oxygen is thought by some to be responsible for the observed cytotoxic effect. Alternatively, there may be direct electron transfer from the photoactivated molecule. The method of van Lier, *Photobiological Techniques*, 216, 85–98 (Valenzo et al. eds. 1991) can be used to confirm the ability of any given compound to generate singlet oxygen effectively, thus making it a good candidate for use in PDT. In addition, the photoactivated forms of porphyrin are able to fluoresce, and this fluorescence can aid in imaging a tumor.

Typical indications known in the art include the diagnosis and destruction of tumor tissue in the form of solid tumors, such as those of bronchial, cervical, esophageal or colon cancer; dissolution of plaques in blood vessels (see, e.g., U.S. Pat. No. 4,512,672, which is hereby incorporated by reference); treatment of topical conditions such as acne, athlete's foot, warts, papilloma and psoriasis; and treatment of biological products, such as blood for transfusion to eliminate infectious agents.

Additionally, when metals such as In or Tc are used, the metallated meso-substituted compounds of the invention have diagnostic use in nuclear medicine. Similarly, when M is Mn(III) or Gd(III), the compounds may be useful in magnetic resonance imaging. These are also applications where, due the variability possible with respect to the substitution patterns, significantly improved biodistribution properties may be achieved by using the compounds of the invention.

The photosensitizers made from the compounds of the invention can be formulated into pharmaceutical compositions for administration to the subject or applied to an in vitro target using techniques generally known in the art. A summary of such pharmaceutical compositions may be found, for example, in Remington's Pharmaceutical Sciences, Mack Publishing Co., Easton, Pa. The compounds of the invention can be used singly or as components of mixtures.

Generally, for the diagnosis or treatment of solid tumors, the compound of the invention, labeled or unlabeled, is administered systemically, such as by injection. Injection may be intravenous, subcutaneous, intramuscular, or even intraperitoneal. Injectables can be prepared in conventional forms, either as liquid solutions or suspensions, solid forms suitable for solution or suspension in a liquid prior to injection, or as emulsions. Suitable excipients are, for example, water, saline, dextrose, glycerol and the like. Of course, these compositions may also contain minor amounts of nontoxic, auxiliary substances, such as wetting or emulsifying agents, pH buffering agents, and so forth.

Systemic administration can be implemented through implantation of a slow release or sustained release system, by suppository, or, if properly formulated, orally. Formulations for these modes of administration are well known in the art, and a summary of such methods may be found, for example, in Remington's Pharmaceutical Sciences (supra).

If treatment is to be localized, such as for the treatment of superficial tumors or skin disorders, the compound can be administered topically using standard topical compositions, such as lotions, suspensions, or pastes.

The quantity of the photosensitizer compound to be administered depends upon the choice of active ingredient, the condition to be treated, the mode of administration, the individual subject, and the judgment of the practitioner. Depending on the specificity of the preparation, smaller or larger doses may be needed. For compositions that are highly specific to target tissues, such as those with a highly specific monoclonal immunoglobulin preparation or a specific receptor ligand, dosages in the range of 0.05–1 mg/kg are suggested. For compositions that are less specific to the target tissue, larger doses, up to 1–10 mg/kg may be needed. The foregoing ranges are merely suggestive, as the number of variables in regard to an individual treatment regime is large, and considerable excursions from these recommended values are not uncommon.

In addition to in vivo use, compounds made from the intermediate iodinated compounds of the invention can be used in the treatment of materials in vitro to destroy harmful viruses or other infectious agents. For example, blood plasma or blood that is to be used for transfusion or banked for future transfusion, can be treated with the compounds of the invention and irradiated to effect sterilization. In addition, biological products such as Factor VIII, which are prepared from biological fluids, can be irradiated in the presence of the compounds of the invention to destroy contaminants.

Synthetic pathways of potential interest that may be pursued with the meso-alkynyl tetramacrocycle of the invention include the formation of meso-ethynyl diphenylporphyrins, followed by a second coupling reaction to another iodinated compound.

The introduction of the meso-alkynyl group usually gives the molecule an amphiphilic character, a property that may be important in the biodistribution of site-specific photo-chemotherapeutics. Further, because the $S^1$ through $S^3$ groups in the three meso-positions can be the same or different, and may themselves be substituted either symmetrically or asymmetrically, the compounds of the invention can be "fine tuned" to produce a desired set of biological effects when administered to a subject in need of PDT. Further still, the invention provides methods for synthesizing these compounds in an efficient manner with relatively few by-products or isomeric impurities. If desired, the product can be subjected to a simple general demetallation procedure as follows:

The metallated version of the desired meso-alkynylated is dissolved in methylene chloride, and a small amount of trifluoroacetic is added. The resulting green solution is stirred for five minutes and poured into water. The organic phase is separated, washed with water, and dried over an anhydrous desiccant. Filtration of the organic phase and evaporation of the solvent gives the corresponding metal-free tetramacrocycle, usually in quantitative yields.

The invention will be further clarified by the following examples, which are intended to be purely illustrative of the invention.

EXAMPLE 1

Iodination of 5,15-Diphenylporphyrin

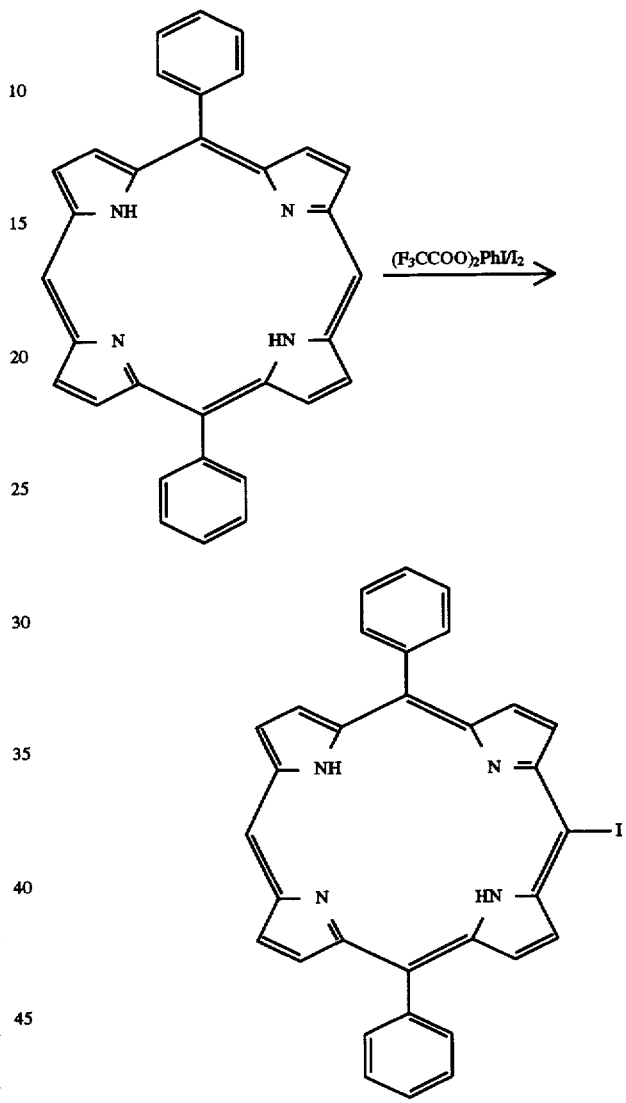

50 mg (0.11 mmol) of 5,15-diphenylporphyrin was dissolved in 50 ml of dry CHCl$_3$. To the stirred solution was added 3 ml of a solution of iodine in chloroform (0.055M). Finally, a solution of 50 mg (0.12 mmol) bis(trifluoroacetoxy)iodobenzene dissolved in 25 ml of chloroform was added dropwise, followed by 200 μl of pyridine. The mixture was stirred at 25° C., in the dark, for one hour. After evaporation of the solvent in vacuo, the residue was chromatographed on silica gel, eluting with 50% 1,1-dichloromethane in hexane to give 44 mg of 10-iodo-5,15-diphenylporphyrin (70% yield). UV-Vis (CH$_2$Cl$_2$): $\lambda_{max}$422, 520, 560, 600, 660 nm; MS (EI) m/e 588(100). Annotated wavelengths for electronic absorption spectrum shown in FIG. 1:

| Wavelength | Absorbance |
|---|---|
| 422 | 1.122314 |
| 518 | 0.086899 |
| 558 | 0.069290 |
| 580 | 0.053253 |
| 606 | 0.050903 |

EXAMPLE 2

Metallation of 10-iodo-5,15-diphenylporphyrin

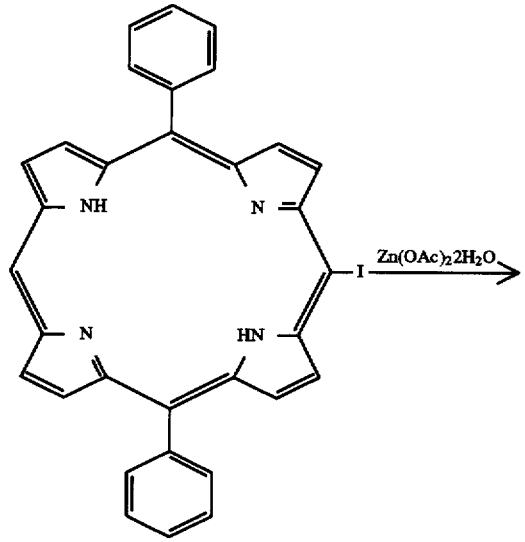

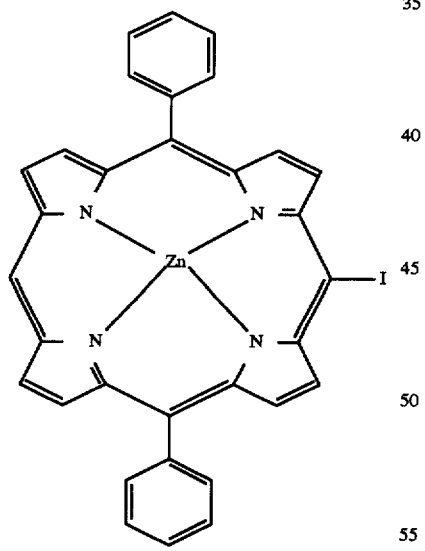

50 mg (85 μmol) of the iodinated starting compound, 10-iodo-5,15-diphenylporphyrin was dissolved in 30 ml of CHCl$_3$, and the stirred solution was brought to reflux under an atmosphere of N$_2$. A solution of 100 mg (0.456 mmol) Zn(OAc)$_2$·H$_2$O in 5 ml of methanol was added, and the mixture was held at reflux for 16 hours. Following evaporation of the solvent in vacuo, the residue was passed through a short column of neutral alumina, eluting with methylene chloride. Evaporation of the solvent gave 48 mg of 10-iodo-5,15-diphenylporphyrin zinc (87% yield).

$^1$H NMR (400 MHz, Pyridine d$_5$) δ=7.74–7.78 (m, 6H); 8.3 (dd, J=6.22, 1.13 Hz, 4H); 9.11 (dd, 4.72, <1 Hz, 4H); 9.48 (d, 4.46 Hz, 2H); 10.03 (d, 4.61 Hz, 2H); 10.36 (s, 1H).

UV-Vis (CH$_2$Cl$_2$): λ$_{max}$ 420, 548 nm; MS (EI) m/e calc'd for C$_{32}$H$_{19}$N$_4$IZn(M$^+$): 649.9946, found: 649.9936.

Figure 2:
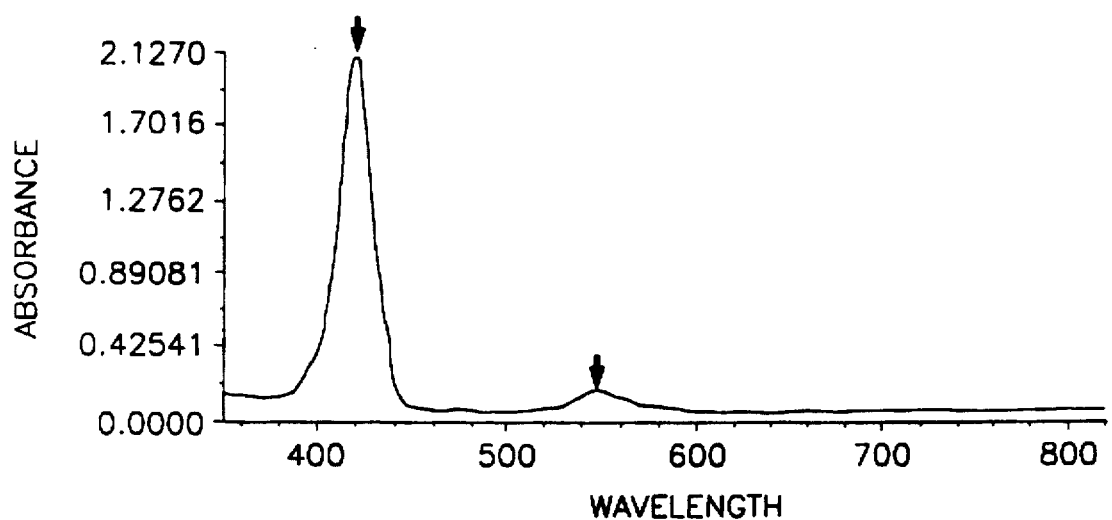
FIG. 2 shows the electronic absorption spectrum for 10-iodo-5,15-diphenylporphyrin zinc.

Annotated wavelengths for electronic absorption spectrum shown in FIG. 2:

| Wavelength | Absorbance |
|---|---|
| 420 | 2.127029 |
| 548 | 0.160812 |

EXAMPLE 3

Alkynylation of 10-iodo-5,15-diphenylporphyrin Zinc

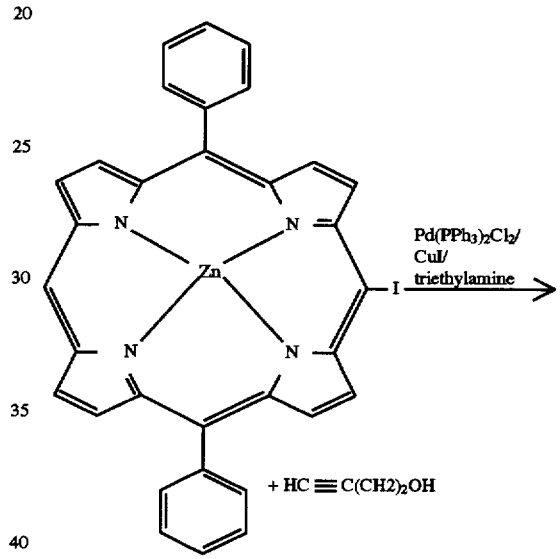

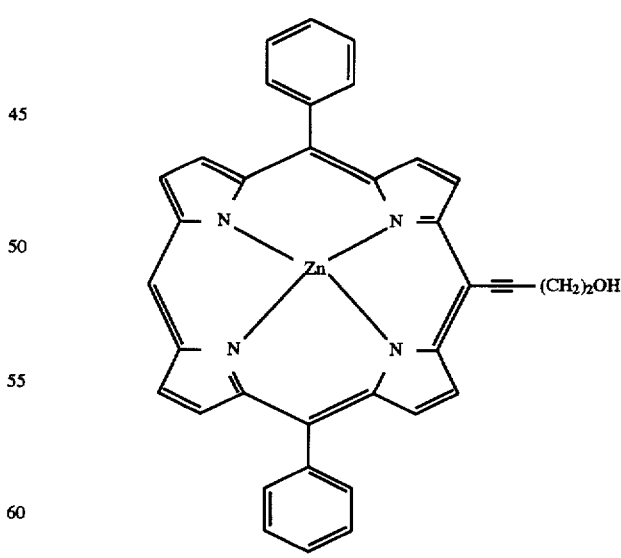

The product compound of Example 2, 10-iodo-5,15-diphenylporphyrin zinc (10 mg; 15.4 mol) was dissolved in 10 ml of dry tetrahydrofuran. Bis(triphenylphosphine)-palladium(II) chloride (2 mg; 2.8 μmol), copper(I) iodide (10 mg; 53 µmol), and triethylamine (100 µmol) were added to the stirred solution. Finally, 34 µmol of the alkyne, HC≡C—(CH$_2$)$_2$—OH, was added, and the mixture was stirred at 25° C. for two hours. The solvent was evaporated off in vacuo, and the residue was chromatographed on silica gel to give the 10-alkynylated-5,15-diphenylporphyrin zinc (89% yield).

$^1$H NMR (400 MHz, CDCl$_3$) δ=2.91 (t, J=6.1 Hz, 2H); 3.75–3.79 (m, 2H); 7.73–7.78 (m, 6H); 8.19 (dd, J=6.24, 1.37 Hz, 4H); 8.95 (dd, J=4.74, <1 Hz, 4H); 9.24 (d, J=4.45 Hz, 2H); 9.55 (d, J=4.54 Hz, 2H); 10.07 (s, 1H);

UV-Vis(CH$_2$Cl$_2$): λ$_{max}$=422, 552, 590 nm; MS m/e calc'd for C$_{36}$H$_{24}$N$_4$OZn (M$^+$): 592.1241, found: 592.1236.

Figure 3:
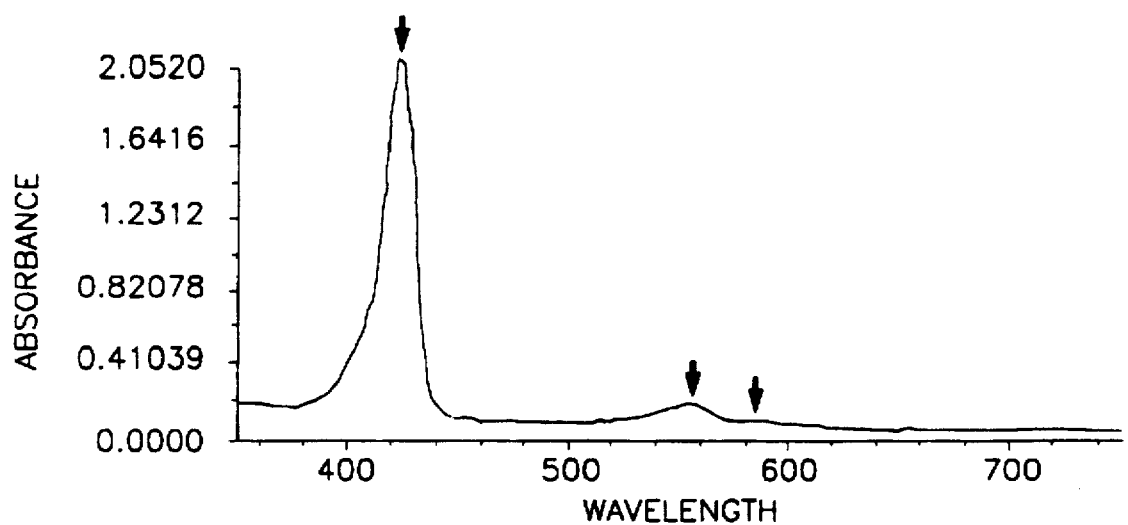
FIG. 3 shows the electronic absorption spectrum for 10-(4-hydroxy-1-butynyl)-5,15-diphenylporphyrin.

Annotated wavelengths for electronic absorption spectrum shown in FIG. 3:

| Wavelength | Absorbance |
|---|---|
| 584 | 0.066940 |
| 552 | 0.149658 |
| 422 | 2.051956 |

EXAMPLE 4

Preparation of Other Meso-alkynyl Tetramacrocycles

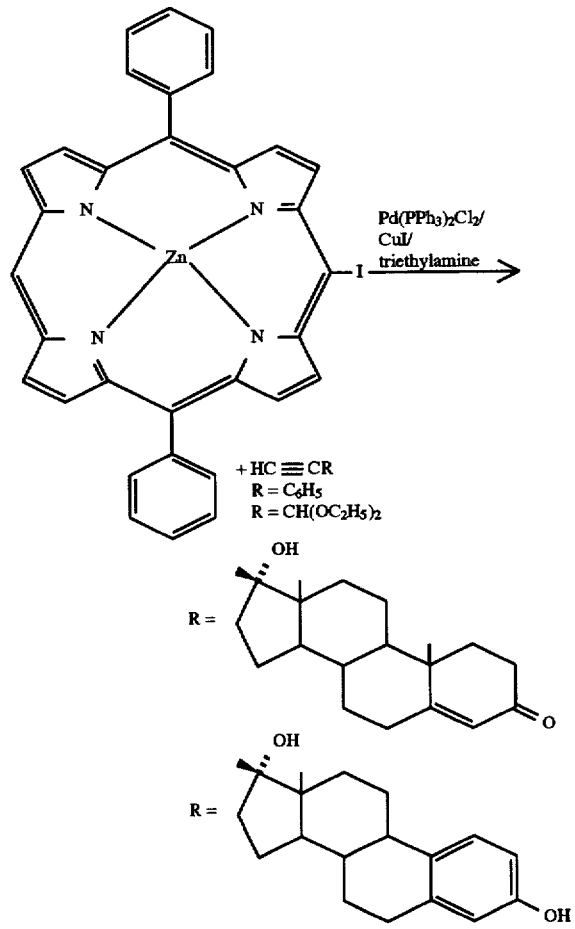

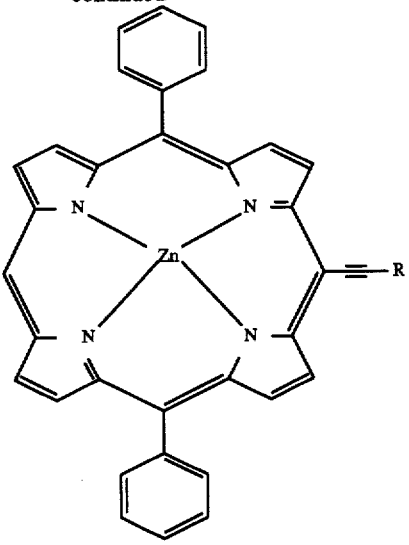

The five compounds above were prepared according to the general alkynylation procedure set forth in Example 3 above. The following data were obtained for each product:

R=C$_6$H$_5$:

Yield=85%; $^1$H NMR (400 MHz, CDCl$_3$) δ=7.54–7.57 (m, 3H); 7.74–7.81 (m, 6H); 8.02 (dd, J=7.31, <1 Hz, 2H); 8.21 (dd, J=7.61, 2 Hz, 4H); 8.98 (d, J=4.46 Hz, 2H); 9.01 (d, J=4.51 Hz, 2H); 9.3 (d, J=4.51 Hz, 2H); 9.84 (d, J=4.68, 2 Hz); 10.15 (s, 1H); UV-Vis (CH$_2$Cl$_2$) λ$_{max}$=432, 558, 600, 634 nm; MS m/e calc'd for C$_{40}$H$_{24}$N$_4$Zn(M$^+$): 624.1292, found: 624.1285.

Figure 4:
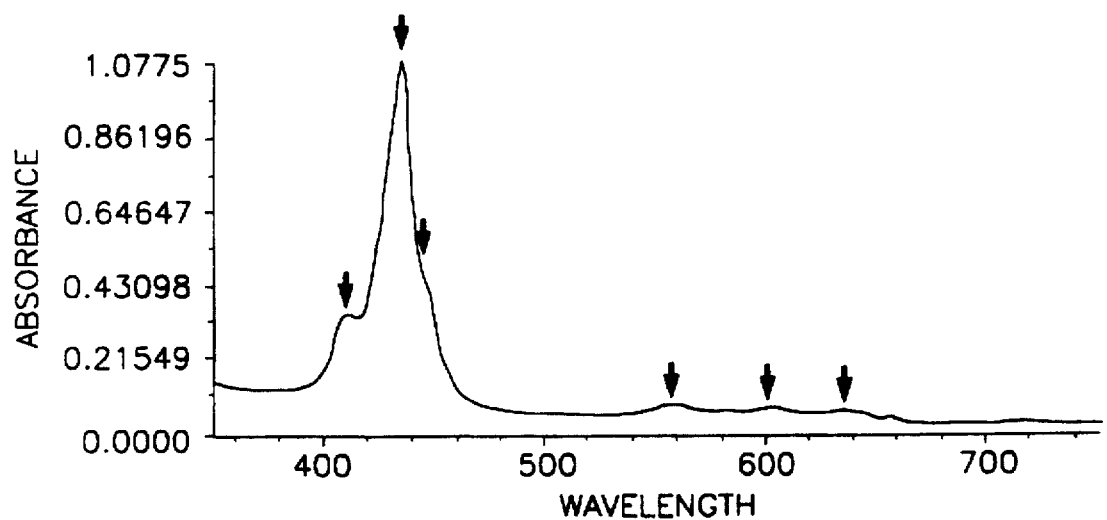
FIG. 4 shows the electronic absorption spectrum for 10-(2-phenyl-1-ethynyl)-5,15-diphenylporphyrin.

Annotated wavelengths for electronic absorption spectrum shown in FIG. 4:

| Wavelength | Absorbance |
|---|---|
| 408 | 0.343811 |
| 432 | 1.077454 |
| 446 | 0.408539 |
| 558 | 0.088120 |
| 600 | 0.080658 |
| 634 | 0.070648 |

R=CH(OC$_2$H$_5$)$_2$:

Yield=61%; $^1$H NMR (400 MHz, CDCl$_3$) δ=1.19 (t, J=7.07 Hz, 6H); 3.52–3.59 (m, 2H); 3.65–3.72 (m, 2H); 5.25 (s, 1H); 7.73–7.77 (m, 6H); 8.19 (dd, J=5.64, 1.37 Hz, 4H); 8.99 (dd, J=5.01, <1 Hz, 4H); 9.32 (d, J=4.59 Hz, 2H); 9.72 (d, J=4.56 Hz, 2H); 10.19 (s, 1H); UV-Vis (CH$_2$Cl$_2$) λ$_{max}$= 422, 552, 584 nm; MS m/e calc'd for C$_{39}$H$_{30}$N$_4$O$_2$Zn(M$^+$): 650.1660, found: 650.1658.

Figure 5:
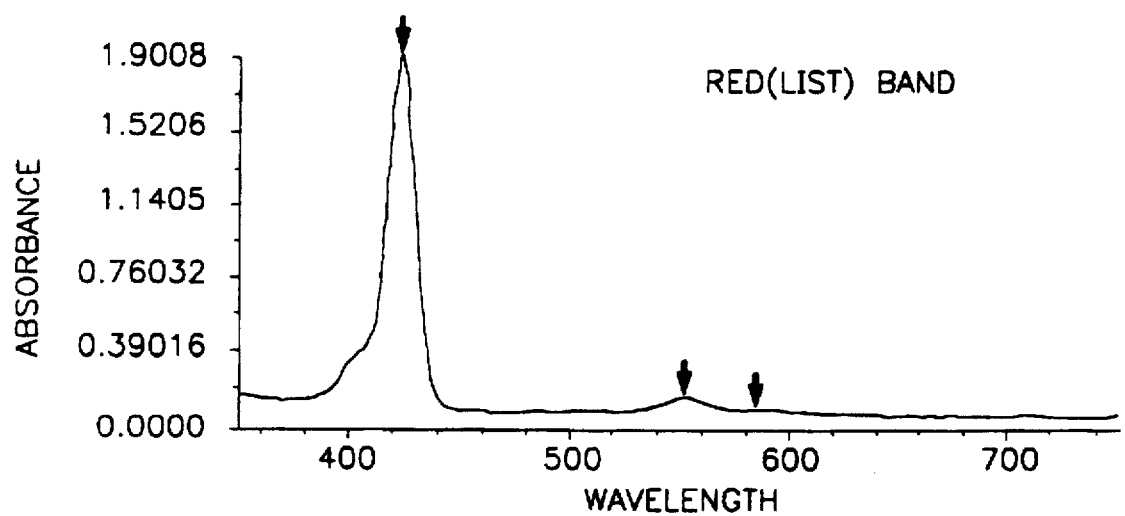
FIG. 5 shows the electronic absorption spectrum for 10-(3,3'-diethoxy-1-propynyl)-5,15-diphenylporphyrin.

Annotated wavelengths for electronic absorption spectrum shown in FIG. 5:

| Wavelength | Absorbance |
|---|---|
| 584 | 0.064743 |
| 552 | 0.128479 |
| 422 | 1.900803 |

R=Si(CH$_3$)$_3$:

Yield=71%; $^1$H NMR (400 MHz, CDCl$_3$) δ=0.59 (s, 9H); 7.73–7.79 (m, 6H); 8.2 (dd, J=5.76, 1.49 Hz, 4H); 8.99 (dd, J=4.55, <1 Hz, 4H); 9.31 (d, J=4.46 Hz, 2H); 9.77 (d, J=4.69 Hz, 2H); 10.17 (s, 1H); UV-Vis (CH$_2$Cl$_2$) $\lambda_{max}$=424, 556 nm; MS m/e calc'd for C$_{37}$H$_{28}$N$_4$SiZn(M$^+$): 620.1375, found: 620.1370.

Figure 6:
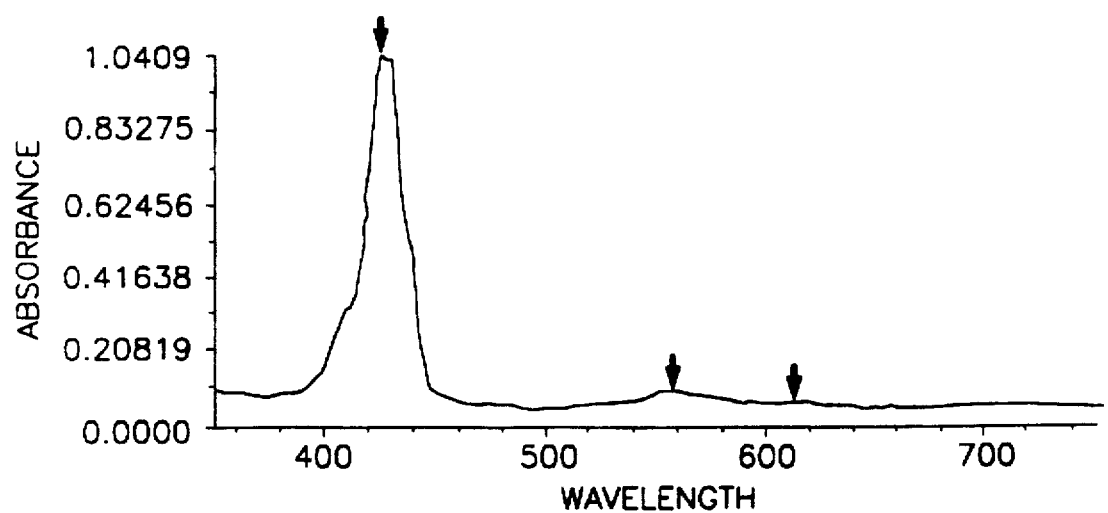
FIG. 6 shows the electronic absorption spectrum for 10-(2-trimethylsilyl-1-ethynyl)-5,15-diphenylporphyrin.

Annotated wavelengths for electronic absorption spectrum shown in FIG. 6:

| Wavelength | Absorbance |
|---|---|
| 424 | 1.039230 |
| 556 | 0.084732 |
| 510 | 0.055023 |

R=testosterone

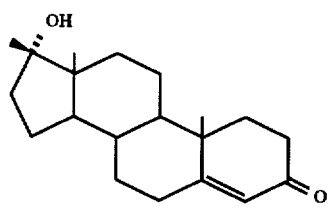

Yield =60%; $^1$H NMR (400 MHz, CDCl$_3$) $\delta$=1.14 (s, 3H); 1.21 (s, 3H); 2.9–3 (m, 2H); 5.56 (s, 1H); 7.73–7.78 (m, 6H); 8.18 (dd, J=6, 1.56 Hz, 4H); 8.98 (d, J=4.44 Hz, 2H); 9.01 (d, J=4.45 Hz, 2H); 9.29 (d, J=4.44 Hz, 2H); 9.68 (d, J=4.67 Hz, 2H); 10.15 (s, 1H); UV-Vis (CH$_2$Cl$_2$) $\lambda_{max}$=424, 554, 592 nm; MS m/e calc'd for C$_{53}$H$_{46}$N$_4$O$_2$Zn(M$^+$): 834.2912, found: 834.2903.

Figure 7:
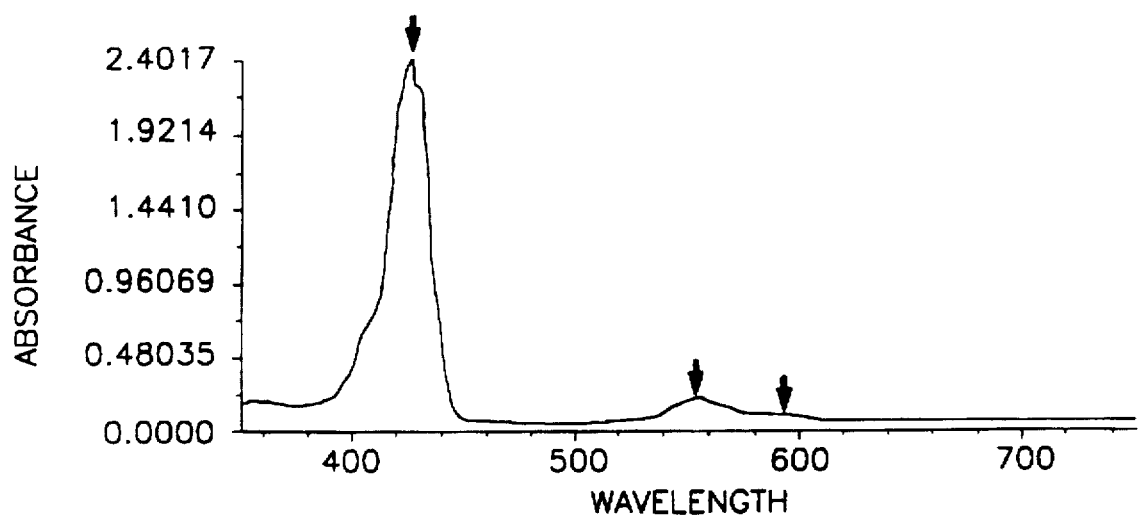
FIG. 7 shows the electronic absorption spectrum for 10-(2-testosterone-1-ethynyl)-5,15-diphenylporphyrin.

Annotated wavelengths for electronic absorption spectrum shown in FIG. 7:

| Wavelength | Absorbance |
|---|---|
| 424 | 2.401733 |
| 554 | 0.206039 |
| 592 | 0.097625 |

R=estradiol

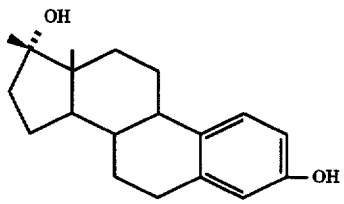

Yield =53%; $^1$H NMR (400 MHz, CDCl$_3$) $\delta$=1.14 (s, 3H); 2.7–3.05 (m, 4H); 4.49 (br s, 1H); 6.52 (d, J=2.34 Hz, 1H); 6.57 (dd, J=8.39, 2.34 Hz, 1H); 7.16 (d, J=8.41 Hz, 1H); 7.75–7.79 (m, 6H); 8.91 (dd, J=7.63, 1.77 Hz, 4H); 9.0 (d, J=4.66 Hz, 2H); 9.02 (d, J=4.66 Hz, 2H); 9.31 (d, J=4.52 Hz, 2H); 9.76 (d, J=4.71 Hz, 2H); 10.17 (s, 1H); UV-Vis (CH$_2$Cl$_2$) $\lambda_{max}$=424, 554, 592 nm; MS m/e calc'd for C$_{53}$H$_{46}$N$_4$O$_2$Zn(M$^+$): 834.2912, found: 834.2903.

Figure 8:
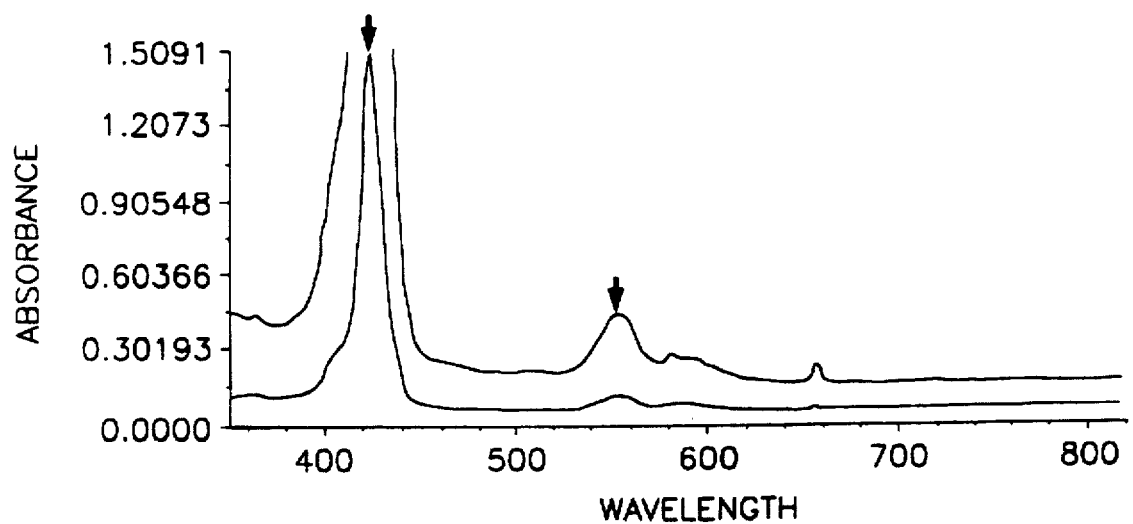
FIG. 8 shows the electronic absorption spectrum for 10-(2-estradiol-1-ethynyl)-5,15-diphenylporphyrin.

Annotated wavelengths for electronic absorption spectrum shown in FIG. 8:

| Wavelength | Absorbance |
|---|---|
| 424 | 1.509140 |
| 554 | 0.415894 |

EXAMPLE 5

Alkynylation with HC≡C—(CH$_2$)$_4$C≡CH

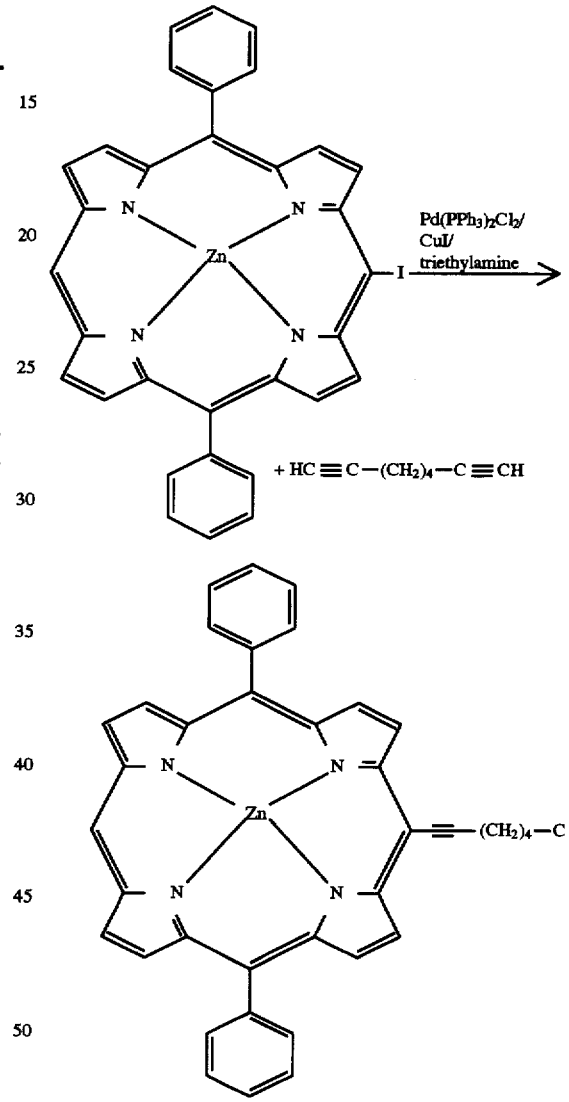

10 mg of starting metallated, meso-iodinated product from Example 3 above was dissolved in dry 10 ml of dry tetrahydrofuran. Bis(triphenylphosphine)palladium(II) chloride (2 mg; 2.8 μmol), copper(I) iodide (10 mg, 53 μmol), and 100 μl of triethylamine were added to the stirred solution. Finally, 1,7-octadiyne (50 μl; 0.377 mmol) was added, and the mixture was stirred at 25° C. for two hours. The solvent was evaporated off in vacuo, and the residue was chromatographed on silica gel to give 10-(1,7-octadiynyl)-5,15-diphenylporphyrin zinc. The yield was 55%.

$^1$H NMR (400 MHz, CDCl$_3$): $\delta$=2–2.12 (m, 5H); 2.94 (t, J=6.77 Hz, 2H); 3.06 (t, J=6.77 Hz, 2H); 7.73–7.79 (m, 6H);

8.21 (dd, J=5.66, 1.9 Hz, 4H); 8.99 (dd, J=4.43, <1 Hz, 4H); 9.31 (d, J=4.51 Hz, 2H); 9.75 (d, J=4.48 Hz, 2H); 10.16 (s, 1H); UV-Vis (CH$_2$Cl$_2$): $\lambda_{max}$=422, 548, 582 nm; MS m/e calc'd for C$_{40}$H$_{28}$N$_4$Zn(M$^+$): 628.1605, found: 628.1601.

Figure 9:
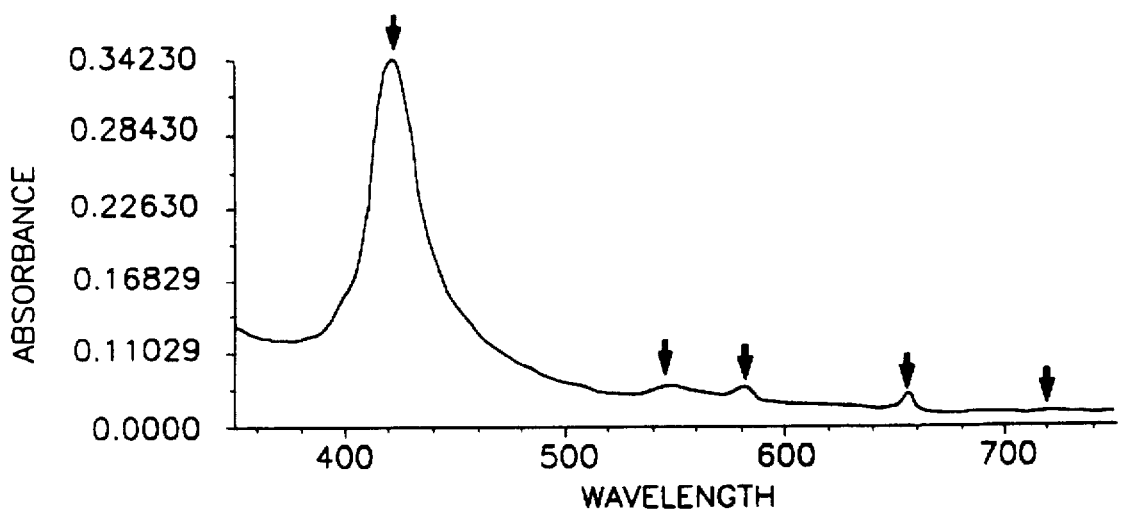
FIG. 9 shows the electronic absorption spectrum for 10-(1,7-octadiynyl)-5,15-diphenylporphyrin.

Annotated wavelengths for electronic absorption spectrum shown in FIG. 9:

| Wavelength | Absorbance |
|---|---|
| 720 | 0.058578 |
| 656 | 0.075485 |
| 582 | 0.081009 |
| 548 | 0.081055 |
| 422 | 0.342300 |

EXAMPLE 6

Demetallation of Alkynylated Product

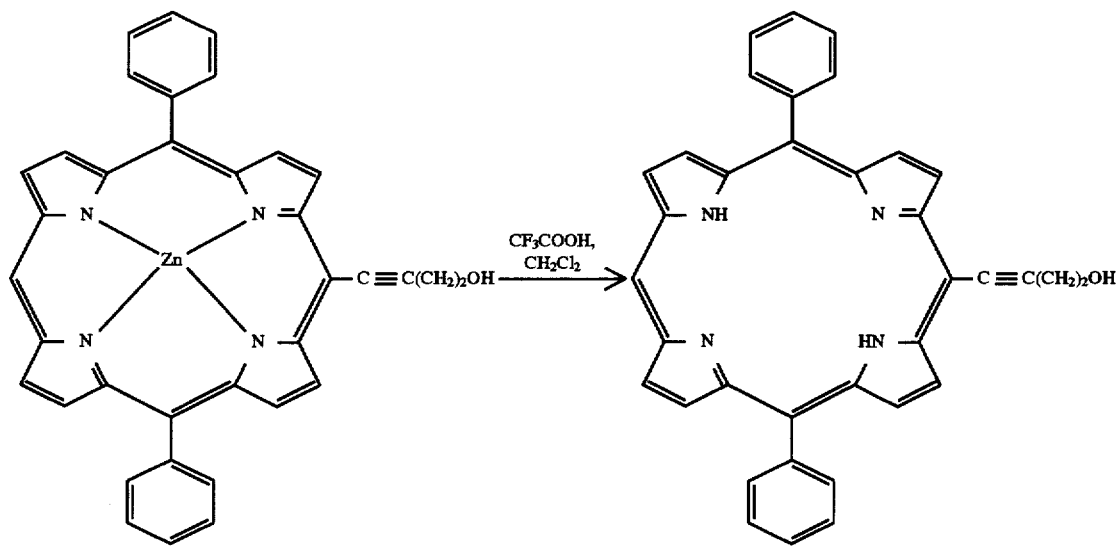

10 μmol of the starting material, 10-(3-hydroxy-1-butynyl)-5,15-diphenylporphyrin zinc was dissolved in 10 ml CH$_2$Cl$_2$, and 50 μl of trifluoroacetic acid was added. The resulting green solution was stirred for five minutes. The mixture was poured into 100 ml water. The organic phase was separated, washed with water (3×100 ml), and dried over anhydrous potassium carbonate. The organic phase was filtered and evaporated to dryness to give the corresponding metal-free 10-(3-hydroxy-1-butynyl)-5,15-diphenylporphyrin in quantitative yield.

We claim:

1. A meso-monoiodo-substituted tetramacrocyclic compound having the formula (I):

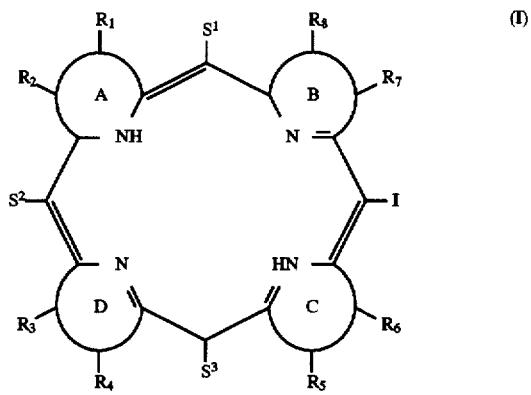

wherein:
each of A tough D is independently a 5-membered, nitrogen-containg ring having the members necessary to complete a porphyrin, chlorin, bacteriochlorin or isobacteriochlorin nucleus;

R$_1$ through are R$_8$ independently a hydrogen atom, a lower alkyl group, a lower alkyl carboxylic acid or acid ester group, keto, hydroxy, nitro, amino, or R$_1$ and R$_2$, R$_3$ and R$_4$, R$_5$ and R$_6$, or R$_7$ and R$_8$, taken together with another ring, ring substituent or meso-substituent, forms a fused 5- or 6-membored ring selected from the group consisting of cyclopentane, furan, thiophene, pyrrole, isopyrrole, 3-isopyrrole pyrazole, 2-isoimidole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiathiazole, 1,2,4-oxdiazole, 1,2,5-oxadiazole, 1,3,4-oxadiazole, 1,2,3-dioxazole, 1,2,4-dioxazole, 1,2,5-oxathiazole, 1,3-oxathiole, benzene, cyclohexane, 1,2-pyran, 1,4-pyran, 1,2-pyrone, 1,4-pyrone, 1,2-dioxin, 1,3-dioxin (dihydro form), pyridine, pyridazine, pyrimidine, pyrazine, piperazine, 1,3,5-triazine, 1,2,4-triazine, 1,2,4-oxazine, 1,3,2-oxazine, o-isoxazine, 1,2,5-oxathiazine, 1,4-oxazine, p-isoxazine, 1,2,6-oxathiazine, 1,3,5,2-oxaciazine, morpholine, azepine, oxepin, thiepin and 1,2,4-diazepine; and each of S$^1$ through S$^3$ is H, substituted or unsubstituted alkyl having about 1 to about 18 carbon atoms, and wherein said alkyl group is substituted by a group selected from the group consisting of a halogen atom, a hydroxy group, thiol, a carbonyl group, a primary amino group, a secondary amino group, a tertiary amino group, a quaternary amino group, nitrile, a phosphate group and a sulfonate group, substituted or unsubstituted cycloalkyl having about 3 to about 7 carbon atoms, and wherein said cycloalkyl group is substituted by a group selected from the group consisting of halogen atom, a hydroxy group, thiol, a carbonyl group, a primary amino group, a secondary amino group, a tertiary amino group, a quaternary amino group, nitrile, a phosphate group and a sulfonate group, a substituted or unsubstituted aromatic ring having about 5 to about 12 carbon atoms, or a substituted or unsubstituted heterocyclic ring selected from the group consisting of furan, thiophene, pyrrole, isopyrrole, 3-isopyrrole, pyrazole, 2-isoimidazole, 1,2,3-triazole, 1,2,4-triazole, 1,2-dithiole, 1,3-dithiole, 1,2,3-oxathiazole, isoxazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxathiazole, 1,3-oxathiazole, benzene, 1,2-pyran, 1,4-pyran, 1,2-pyrone, 1,4-pyrone, 1,2-dioxin, 1,3-dioxin, pyridine, N-alkyl pyridinium, pyrdazine, pyrimidine, pyrazine, 1,3,5-triazine, 1,2,4-triazine, 1,2,3-triazine, 1,2,4-oxazlne, 1,3,2-oxazine, 1,3,6-oxazine, 1,4-oxazine, o-isoxazine, p-isoxazine, 1,2,5-oxathiazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, naphthalene, 1,2-benzopyran, 1,2-benzopyrone, 1,4-benzopyrone, 2,1-benzopyrone, 2,3-benzopyrone, quinoline, isoquinoline, 1,2-benzodiine, 1,3-benzodiazine, naphthyridine, pyrido[3,4-b]-pyridine, pyrido[3,2-b]-pyridine, pyrido[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, anthracene, phenanthrene, carbazole, xanthene, acridine and purine.

2. The compound of claim 1 wherein A through D and $R_1$ through $R_8$ have the members necessary to make a porphyrin, chlorin, bacteriochlorin, benzochlorin, hydroxychlorin or hydroxybacteriochlorin nucleus.

3. The compound of claim 1 wherein $R_1$ through $R_8$ are independently hydrogen, methyl, ethyl, or lower alkyl esters.

4. The compound of claim 1 wherein $S^1$ through $S^3$ are selected from the group consisting of phenyl, naphthyl, pyridinyl, lower N-alkyl pyridinium salts, indolyl, pyrazinyl, pyrimidinyl, imidazolyl, triazolyl, pyrrolyl, pyrazolyl, pyridazinyl, indolizinyl, furanyl, and thiophenyl.

5. The compound of claim 1 wherein at least one of S through $S^3$ has the structure:

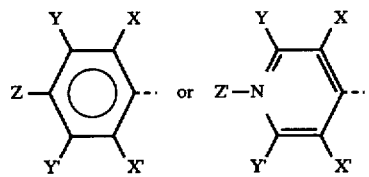

wherein X, X', Y, Y' and Z are independently hydrogen, halogen, lower alkyl, lower alkoxy, hydroxy, carboxylic acid or acid salt, carboxylic acid ester, sulfonic acid or acid salt, sulfonic acid ester, phosphonic acid, phosphato, phosphate ester, substituted or unsubstituted amino, cyano, nitro, or a biologically active group selected from sugar derivatives, amino acid derivatives, peptides and nucleosides derivatives, and Z' is hydrogen or lower alkyl.

6. The compound of claim 5 wherein X, X', Y, Y' and Z are selected from the group consisting of hydrogen, methyl, ethyl, t-butyl, methoxy, hydroxy, OR where R is an alkyl group or a fatty acid group having from 6 to 18 carbon atoms, fluoro, chloro, iodo, bromo, —C(O)—OCH$_3$, cyano, nitro, or a ligand specific for a biological receptor.

7. The compound of claim 5 wherein X, X', Y and Y' are each hydrogen, and Z is selected from the group consisting of hydrogen, halogen, lower alkyl, lower alkoxy, hydroxy, carboxylic acid or acid salt, carboxylic acid ester, sulfonic acid ester, sulfonic acid or acid salt, phosphonic acid, phosphato, phosphate ester, nitro, amino, cyano, and a biologically active group.

8. The compound of claim 5 wherein at least one of X, X', Y, Y' and Z is a biologically active group or a substituent that increases the amphiphilic nature of the molecule.

9. The compound of claim 1 wherein each of $S^1$ through $S^3$ is selected from the group consisting of phenyl, pyridinyl, lower N-alkyl pyridinium salts, indolyl, pyrazinyl, pyrimidinyl, imidazolyl, triazolyl, pyrrolyl, pyrazolyl, pyridazinyl, indolizinyl, furanyl, and thiophenyl.

10. The compound of claim 9 wherein at least two of $S^1$ through $S^3$ are identical.

11. A method for synthesizing a meso-monoiodo-substituted tetramacrocyclic compound having the formula (I):

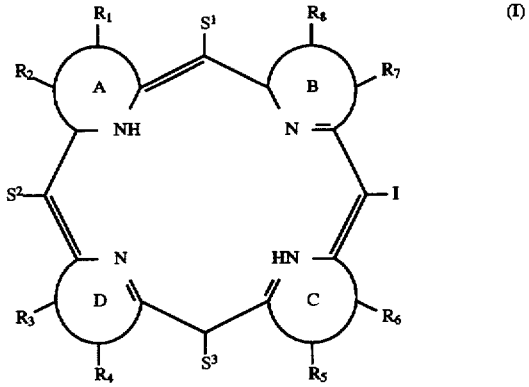

wherein
each of A through D is independently a 5-membered, nitrogen-containing ring having the members necessary to complete a porphyrin, chlorin, bacteriochlorin or isobacteriochlorin nucleus;

$R_1$ through $R_6$ are independently a hydrogen atom, a lower alkyl group, a lower alkyl carboxylic acid or acid ester group, keto, hydroxy, nitro, amino, or a group that, taken together with another ring, ring substituent or meso-substituent, forms a fused 5- or 6-membered ring; and S¹ throuh S³ are H, substituted or unsubstituted alkyl groups, substituted or unsubstituted cycloalkyl groups, substituted or unsubstituted aromatic rings, or substituted or unsubstituted heterocyclic rings, which may be the same or different, comprising the step of treating a porphyrin having the formula (II):

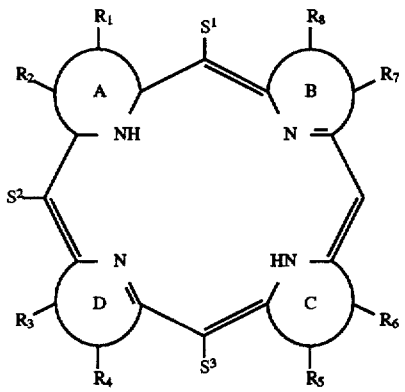

with an iodinating agent to form the tetramacrocyclic compound of formula (I).

12. The method of claim 11 wherein at least one of A through D and R₁ through R₈ have the members necessary to make a porphyrin, chlorin, bacteriochlorin, benzochlorin, hydroxychlorin or hydroxybacteriochlorin nucleus.

13. The method of claim 11 wherein R₁ through R₈ are independently hydrogen, methyl, ethyl, or lower alkyl esters.

14. The method of claim 11 wherein at least one of S through S³ has the structure:

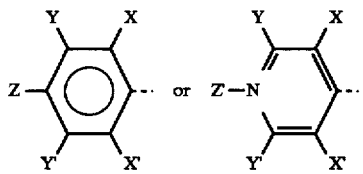

wherein X, X', Y, Y' and Z are independently hydrogen, halogen, lower alkyl, lower alkoxy, hydroxy, carboxylic acid or acid salt, carboxylic acid ester, sulfonic acid or acid salt, sulfonic acid ester, phosphonic acid, phosphato, phosphate ester, substituted or unsubstituted amino, cyano, nitro, or a biologically active group, and Z' is hydrogen or lower alkyl.

15. The method of claim 14 wherein at least one of X, X', Y, Y' and Z is a biologically active group or a group that increases the amphiphilic nature of the molecule.

16. The method of claim 11 wherein said iodinating agent is selected from the group consisting of bis(trifluoroacetoxy) iodobenzene, I₂, N-iodosuccinimide, diacetoxyphenyl iodine, silver triiodoacetate, tris(triiodoacetoxy) thallium, and combinations thereof.

17. The method of claim 11 wherein said treating step takes place in an organic solvent is selected from the group consisting of chloroform, pyridine, dichloromethane, 1,2-dichloroethane, tetrahydrofuran, acetonitrile and diethyl ether.

18. The method of claim 11 wherein said treating step is carried out in darkness.

19. The method of claim 11 wherein said treating step takes place at room temperature.

20. The method of claim 11 wherein said treating step takes place in less than two hours.

21. A method for synthesizing a meso-alkynyl tetramacrocyclic compound having the formula (III):

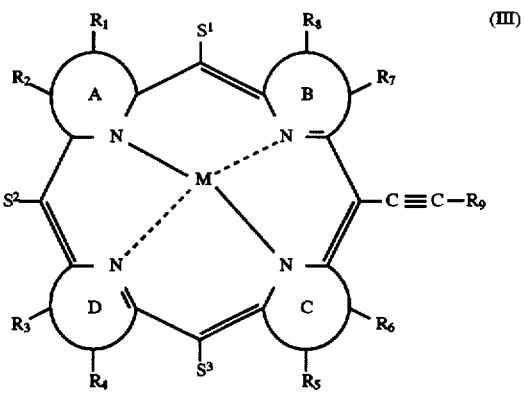

wherein M is a metal selected from the group consisting of Ni(II), Cu(II), Zn, Sn, Ge, Si, Ga, Al, Mn(III), Gd(III), In and Tc;

each of A through D is independently a 5-membered, nitrogen-containing ring having the members necessary to complete a porphyrin, chlorin, bacteriochlorin or isobacteriochlorin nucleus;

R₁ through R₈ are independently a hydrogen atom, a lower alkyl group, a lower alkyl carboxylic acid or acid ester group, keto, hydroxy, nitro, amino, or a group that, taken together with another ring, ring substituent or meso-substituent, forms a fused 5- or 6-membered ring;

S¹ through S³ are H, substituted or unsubstituted alkyl groups, substituted or unsubstituted cycloalkyl groups, or substituted or unsubstituted aromatic rings, or substituted or unsubstituted heterocyclic rings, which may be the same or different; and R₉ is an organometallic radical, a substituted or unsubstituted alkyl group having from 1 to 30 carbon atoms, aromatic, heterocyclic, or a biological substrate;

comprising the steps of:

a. treating a tetramacrocyclic compound having the formula (II):

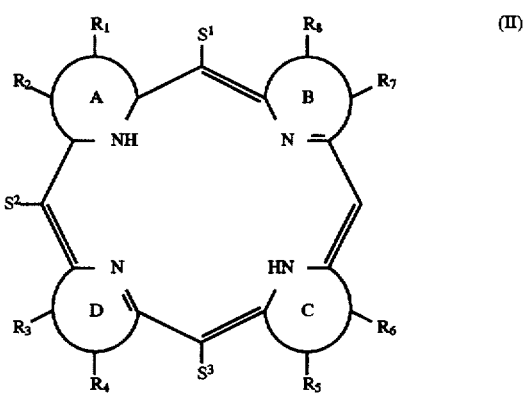

with an iodinating agent to form the corresponding meso-monoiodo-substituted compound of formula (I):

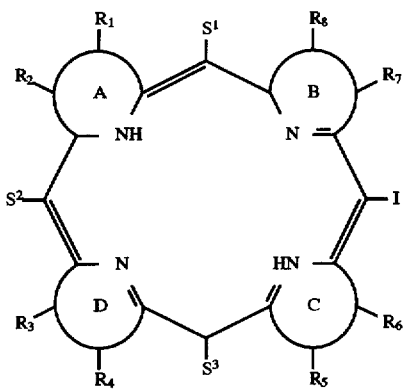

(I)

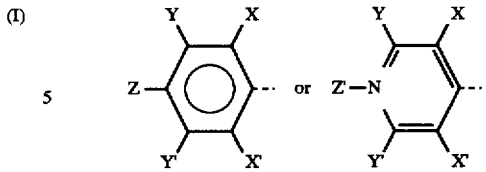

b. metallating said meso-monoiodo-substituted compound to form the corresponding metallated compound; and b. alkynylating said metallated compound in the presence of an alkyne having the formula

HC≡CH—R$_9$ to give the meso-alkynyl tetramacrocyclic compound of formula (III).

22. The method of claim 20 wherein at least one of A through D and R$_1$ through R$_8$ have the members necessary to make a porphyrin, chlorin, bacteriochlorin, benzochlorin, hydroxychlorin or hydroxybacteriochlorin nucleus.

23. The method of claim 20 wherein M is Zn.

24. The method of claim 20 wherein at least one of A through D and R$_1$ through R$_8$ have the members necessary to make a porphyrin, chlorin, bacteriochlorin, benzochlorin, hydroxychlorin or hydroxybacteriochlorin nucleus.

25. The method of claim 20 wherein R$_1$ through R$_8$ are independently hydrogen, methyl, ethyl, or lower alkyl esters.

26. The method of claim 20 wherein R$_9$ is selected from the group consisting of SiMe$_3$, substituted or unsubstituted phenyl, pyridyl, imidazolyl, pyrimidinyl, pyrazinyl, pyrrolyl, thiophenyl, furanyl, and biological substrates.

27. The method of claim 20 wherein at least one of S$^1$ through S$^3$ has the structure:

wherein X, X', Y, Y' and Z are independently hydrogen, halogen, lower alkyl, lower alkoxy, hydroxy, carboxylic acid or acid salt, carboxylic acid ester, sulfonic acid or acid salt, sulfonic acid ester, phosphonic acid, phosphato, phosphate ester, substituted or unsubstituted amino, cyano, nitro, or a biologically active group, and Z' is hydrogen or lower alkyl.

28. The method of claim 25 wherein at least one of X, X', Y, Y' and Z is a biologically active group or a group that increases the amphiphilic nature of the molecule.

29. The method of claim 20 wherein said iodinating agent is selected from the group consisting of bis(trifluoroacetoxy) iodobenzene, I$_2$, N-iodosuccinimide, diacetoxyphenyl iodine, silver triiodoacetate, tris(triiodoacetoxy) thallium, and combinations thereof.

30. The method of claim 29 wherein said treating step a. comprises treating the compound of formula (II) with bis (trifluoroacetoxy)iodobenzene in the presence of I$_2$.

31. The method of claim 20 wherein said treating step a. takes place at room temperature and in the dark.

32. The method of claim 20 wherein said metallating step b. comprises treating said meso-monoiodo-substituted compound with a metallating agent selected from the group consisting of Zn(OAc)$_2$·H$_2$O, Ga(OAc)$_3$, Cu(OAc)$_2$, Ni(OAc)$_2$, GeCl$_4$, Gd(OAc)$_3$, AlCl$_3$, SnCl$_2$, SnCl$_4$, Mn(OAc)$_2$, SiCl$_4$.

33. The method of claim 20 wherein, in said alkynylating step c., said corresponding metallated compound is treated of said alkyne in the presence of a catalyst.

34. The method of claim 33 wherein said catalyst is bis(triphenylphosphine)palladium(II) chloride/copper(I) iodide.

* * * * *

UNITED STATES PATENT AND TRADEMARK OFFICE
CERTIFICATE OF CORRECTION

PATENT NO. : 5,703,230
DATED : December 2, 1997
INVENTOR(S) : BOYLE et al.

It is certified that error appears in the above-indentified patent and that said Letters Patent is hereby corrected as shown below:

column 28, line 65: "R6" should read --R8--;
    column 31, line 20: "b." should read --c.--;
    column 31, line 27: "claim 20" should read --claim 21--;
    column 31, line 31: "claim 20" should read --claim 21--;
    column 31, line 32: "claim 20" should read --claim 23--;
    column 31, line 36: "claim 20" should read --claim 21--;
    column 31, line 38: "claim 20" should read --claim 21--;
    column 31, line 42: "claim 20" should read --claim 21--;
    column 32, line 19: "claim 20" should read --claim 21--;
    column 32, line 27: "claim 20" should read --claim 21--;
    column 32, line 29: "claim 20" should read --claim 21--; and
    column 32, line 35: "claim 20" should read --claim 21--.

Signed and Sealed this

Twelfth Day of October, 1999

Attest:

Q. TODD DICKINSON

*Attesting Officer*      *Acting Commissioner of Patents and Trademarks*